US007323561B2

(12) United States Patent
Lindsey et al.

(10) Patent No.: US 7,323,561 B2
(45) Date of Patent: Jan. 29, 2008

(54) METAL COMPLEXATION OF 1-ACYLDIPYRROMETHANES AND PORPHYRINS FORMED THEREFROM

(75) Inventors: Jonathan S. Lindsey, Raleigh, NC (US); Kannan Muthukumaran, Raleigh, NC (US); Duddu S. Sharada, Tamil Nadu (IN); Ana Z. Muresan, Raleigh, NC (US); W. Justin Youngblood, State College, PA (US)

(73) Assignee: North Carolina State University, Raleigh, NC (US)

( * ) Notice: Subject to any disclaimer, the term of this patent is extended or adjusted under 35 U.S.C. 154(b) by 574 days.

(21) Appl. No.: 11/020,901

(22) Filed: Dec. 23, 2004

(65) Prior Publication Data

US 2006/0142562 A1 Jun. 29, 2006

(51) Int. Cl.
C07B 47/00 (2006.01)
(52) U.S. Cl. ...................................... 540/145
(58) Field of Classification Search ............... 540/145
See application file for complete search history.

(56) References Cited

U.S. PATENT DOCUMENTS

| | | | |
|---|---|---|---|
| 4,618,509 A | 10/1986 | Bulkowski | |
| 5,004,811 A | 4/1991 | Bommer et al. | |
| 5,093,349 A | 3/1992 | Pandey et al. | |
| 5,145,863 A | 9/1992 | Dougherty et al. | |
| 5,241,062 A | 8/1993 | Wijesekera et al. | |
| 5,280,183 A | 1/1994 | Batzel et al. | |
| 5,330,741 A | 7/1994 | Smith et al. | |
| 5,424,974 A | 6/1995 | Liu et al. | |
| 5,441,827 A | 8/1995 | Gratzel et al. | |
| 6,212,093 B1 | 4/2001 | Lindsey | |
| 6,232,547 B1 | 5/2001 | Meissner et al. | |
| 6,420,648 B1 | 7/2002 | Lindsey | |
| 6,559,374 B2 | 5/2003 | Lindsey et al. | |

(Continued)

FOREIGN PATENT DOCUMENTS

EP 0 780 391 A2 6/1997

(Continued)

OTHER PUBLICATIONS

U.S. Appl. No. 10/641,412, filed Aug. 15, 2003, Lindsey et al.

(Continued)

*Primary Examiner*—James O. Wilson
*Assistant Examiner*—Paul V. Ward
(74) *Attorney, Agent, or Firm*—Myers Bigel Sibley & Sajovec, P.A.

(57) ABSTRACT

A first aspect of the invention is a method of making a porphyrin-metal complex, comprising: (a) providing a first reagent selected from the group consisting of 1-acyldipyrromethanes, 1-acyldipyrrins, dipyrromethane-1-carbinols 1,9-diacyldipyrromethanes and 1,9-diacyldipyrrins; and then (b) condensing the first reagent with either itself (in the case of 1-acyldipyrromethanes, 1-acyldipyrrins, and dipyrromethane-1-carbinols) or a dipyrromethane (in the case of 1,9-diacyldipyrromethanes and 1,9-diacyldipyrrins) in a reaction mixture comprising a solvent and a second reagent selected from the group consisting of palladium and copper complexes to produce the porphyrin-metal complex (with the metal being palladium or copper). In preferred embodiments of the foregoing, the reaction mixture further comprises a base such as KOH or NaH.

39 Claims, 1 Drawing Sheet

U.S. PATENT DOCUMENTS

| | | | |
|---|---|---|---|
| 6,603,070 B2 | 8/2003 | Lindsey et al. | |
| 6,642,376 B2 | 11/2003 | Lindsey et al. | |
| 2003/0096978 A1 | 5/2003 | Lindsey et al. | |

FOREIGN PATENT DOCUMENTS

| | | |
|---|---|---|
| WO | WO 98/50393 | 11/1998 |
| WO | WO 00/11725 | 3/2000 |
| WO | WO 02/092601 | 11/2002 |

OTHER PUBLICATIONS

Albery, W. John; Development of Photogalvanic Cells for Solar Energy Conversion, *Acc. Chem. Res.*, 15:142-148 (1982).

Bach et al.; Solid-State Dye-Sensitized Mesoporous $TiO_2$ Solar Cells with High Photon-to-Electron Conversion Efficiencies, *Nature*, 395:583-585 (Oct. 1998).

Balasubramanian, Thiagarajan, et al, Rational Synthesis of β-Substituted Chlorin Building Blocks, *J. Org. Chem.*, vol. 65, pp. 7919-7929 (2000).

Brune, Daniel C., et al., Some Newly Observed Correlations Between Structure and Photochemical Activity in Chlorophyllin a and Several Derivatives, *Archives of Biochemistry and Biophysics*, vol. 163, pp. 552-560 (1974).

Cho, Won-Seob, et al., Rational Synthesis of Trans-Substituted Porphyrin Building Blocks Containing One Sulfur or Oxygen Atom in Place of Nitrogen at a Designated Site, *The Journal of Organic Chemistry*, vol. 64, No. 21, pp. 7890-7901 (1999).

Fungo, et al., Synthesis of porphyrin dyads with potential use in solar energy conversion, *J. Mater. Chem*, vol. 10, pp. 645-650 (2000).

Geier, III, G. Richard, et al., A Survey of Acid Caqtalysts for Use in Two-Step, One-Flask Syntheses of Meso-Substituted Porphyrinic Macrocycles, *Organic Letters*, vol. 2 No. 12, pp. 1745-1748 (2000).

Gryko et al.; "Parallel synthesis of *meso*-substituted corroles and *meso*-substituted [22]pentaphyrins(1.1.1.0.0) from diacyldipyrromethanes" *J. Porphyrins Phthalocyanines* 7 239-248 (2003).

Gryko, et al., Rational Synthesis of Meso-Substituted Porphyrins Bearing One Nitrogen Heterocyclic Group, *J. Org. Chem.*, vol. 65, pp. 2249-2252 (2000).

International Search Report for International Application No. PCT/US02/29783 dated Jul. 21, 2003.

Kamogawa, Kiroyoshi, Preparation of Chlorophyll Polymer, *Polymer Letters*, vol. 10, pp. 711-713 (1972.

Kuciauskas et al.; An Artificial Photosynthetic Antenna-Reaction Center Complex,*J. Am. Chem. Soc.*, 121(37):8604-8614 (1999).

Lee et al., Synthesis of Partially Deuterated Porphyrins, *Bull. Korean Chem. Soc.*, vol. 17, No. 3:215-17 (1996).

Lee, Chang-Hee, et al., Synthetic Approaches to Regioisomerically Pure Porphyrins Bearing Four Different meso-Substituents, *Tetrahedron*, vol. 51, No. 43, pp. 11645-11672 (1995).

Li et al.; Efficient Synthesis of Light-Harvesting Arrays Composed of Eight Porphyrins and One Phthalocyanine, *J. of Org. Chem.*, 64(25):9101-9108 (1999).

Littler, Benjamin J., et al., Investigation of Conditions Giving Minimal Scrambling in the Synthesis of trans-Porphyrins from Dipyrromethanes and Aldehydes, *The Journal of Organi Chemistry*, vol. 64, No. 8, pp. 2864-2872 (1999).

Moss et al.; Sensitization of Nanocrystalline $TiO_2$ by Electropolymerized Thin Films, *Chem. Mater.*, 10(7):1748-1750 (1998).

O'Regan et al.; A Low-Cost, High-Efficiency Solar Cell Based on Dye-Sensitized Colloidal $TiO_2$ Films, *Nature*, 353:737-739 (Oct. 1991).

Parkinson et al.; Recent Advances In High Quantum Yield Dye Sensitization of Semiconductor Electrodes, *Electrochimica Acta.*, 37(5):943-948 (1992).

Rao et al.; "Rational Syntheses of Porphyrins Bearing up to Four Different Meso Substituents" *J. Org. Chem.* 2000 65, 7323-7344 (2000).

Schon et al.; Efficient Organic Photovoltaic Diodes Based on Doped Pentacene, *Nature*, 403:408-410 (Jan. 27, 2000).

Strachan et al.; Rational Synthesis of Meso-Substituted Chlorin Building Blocks, *J. of Org. Chem.*, 65(10):3160-3172 (2000).

Taniguchi, Shozo, et al., A Facile Route to Tripyrrane from 2,5-Bix(hydroxymethyl)pyrrole and the Improved Synthesis of Porphine by the "3+1" Approach, *Synnlett*, vol. 1, pp. 73-74 (1999).

Wagner et al.; A Molecular Photonic Wire, *J. Am. Chem. Soc.*, 116:9759-9760 (1994).

Wagner et al.; Soluble Synthetic Multiporphyrin Arrays. 1. Modular Design and Synthesis, *J. Am. Chem. Soc.*, 118(45):11166-11180 (1996).

Wallace, David M., et al., Stepwise Syntheses of Unsymmetrical Tetra-Arylporphyrins, Adaptation of the MacDonald Dipyrrole Self-Condensation Methodology, *Tet. Let.*, vol. 31, No. 50, pp. 7265-7268 (1990).

METAL COMPLEXATION OF 1-ACYLDIPYRROMETHANES AND PORPHYRINS FORMED THEREFROM

This invention was made with government support under grant number GM36238 from the National Institutes of Health. The Government has certain rights to this invention.

RELATED APPLICATIONS

This application is related to J. Lindsey et al., A Boron Complexation Strategy for Use in Manipulating 1-Acyldipyrromethanes, U.S. patent application Ser. No. 10/872,321, filed Jun. 18, 2004; J. Lindsey et al., Facile Synthesis of 1,9-Diacyldipyrromethanes; U.S. patent application Ser. No. 10/164,181, filed Sep. 3, 2003, and J. Lindsey et al., Methods of Making Porphyrins and Related Compounds with Lewis Acids US Patent Application Publn. No. US 2003/0096978, the disclosures of which are incorporated by reference herein in their entirety.

FIELD OF THE INVENTION

The present invention concerns methods for making porphyrinic macrocycles.

BACKGROUND OF THE INVENTION

Pyrroles that bear α-acyl groups (such as pyrrole-2-carboxaldehyde) are known to form coordination complexes with ketones (e.g., acetylacetone) and metals such as copper (II), nickel(II), palladium(II), or platinum(II).[1-6] The typical reaction conditions employ the 2-acylpyrrole and the metal salt in refluxing ethanol. As part of a study aimed at developing a non-chromatographic method for purifying 1-acyldipyrromethanes (which contain the α-acylpyrrole motif), we screened a variety of metal reagents for formation of stable complexes of 1-acyldipyrromethanes. Dialkylboron reagents were found to serve exceptionally well as complexation aids in the isolation of 1-acyldipyrromethanes from the crude acylation mixture.[7] In the course of this work, we made the surprising finding that some metal reagents, particularly those containing palladium and to a lesser extent copper, result in direct conversion of the acyldipyrromethane to the metalloporphyrin.

Palladium porphyrins are of interest owing to their high yield of intersystem crossing and long-lifetime of the resulting triplet state in diverse media. Palladium porphyrins have been used in diverse applications, including luminescent markers,[8] oxygen sensors,[9] sensitizers of singlet oxygen formation,[10] and in photoinduced protein cross-linking.[11] The first synthesis of PdTPP was reported in 1959.[12] Palladium porphyrins are typically prepared by metalation of the free base porphyrin using Pd(OAc)$_2$ in refluxing benzonitrile[13] or in CH$_2$Cl$_2$/MeOH at room temperature.[10]

SUMMARY OF THE INVENTION

A first aspect of the invention is a method of making a porphyrin-metal complex, comprising: (a) providing a first reagent selected from the group consisting of 1-acyldipyrromethanes, 1-acyldipyrrins, and dipyrromethane-1-carbinols; and then (b) condensing the first reagent with itself in a reaction mixture comprising a solvent and a second reagent selected from the group consisting of palladium and copper complexes to produce a porphyrin-metal complex, wherein said metal is palladium or copper.

A second aspect of the present invention is a method of making a porphyrin-metal complex, comprising: (a) providing a first reagent selected from the group consisting of 1,9-diacyldipyrromethanes and 1,9-diacyldipyrrins; and then (b) condensing the first reagent with a dipyrromethane in a reaction mixture comprising a solvent and a a second reagent selected from the group consisting of palladium and copper complexes to produce a porphyrin-metal complex, wherein said metal is palladium or copper.

In preferred embodiments of the foregoing, the reaction mixture further comprises a base such as KOH or NaH.

In preferred embodiments of the foregoing, the reaction mixture has a pH of at least 7.

In certain embodiments of the foregoing, the condensing step is carried out in the presence of an oxidizing agent such as ambient oxygen.

The foregoing and other objects and aspects of the present invention are explained in greater detail in the drawings herein and the specification set forth below.

BRIEF DESCRIPTION OF THE DRAWINGS

FIG. 1A. The effect of concentration on the self-condensation of 1-acyldipyrromethane 2a yielding the palladium porphyrin. The reaction was carried out for 1 h in refluxing ethanol exposed to air at reflux containing KOH and Pd(CH$_3$CN)$_2$Cl$_2$. The concentrations of KOH and Pd(CH$_3$CN)$_2$Cl$_2$ were altered as required to maintain fixed ratios with respect to the concentration of 2a.

DETAILED DESCRIPTION OF THE PREFERRED EMBODIMENTS

Figure 1A:
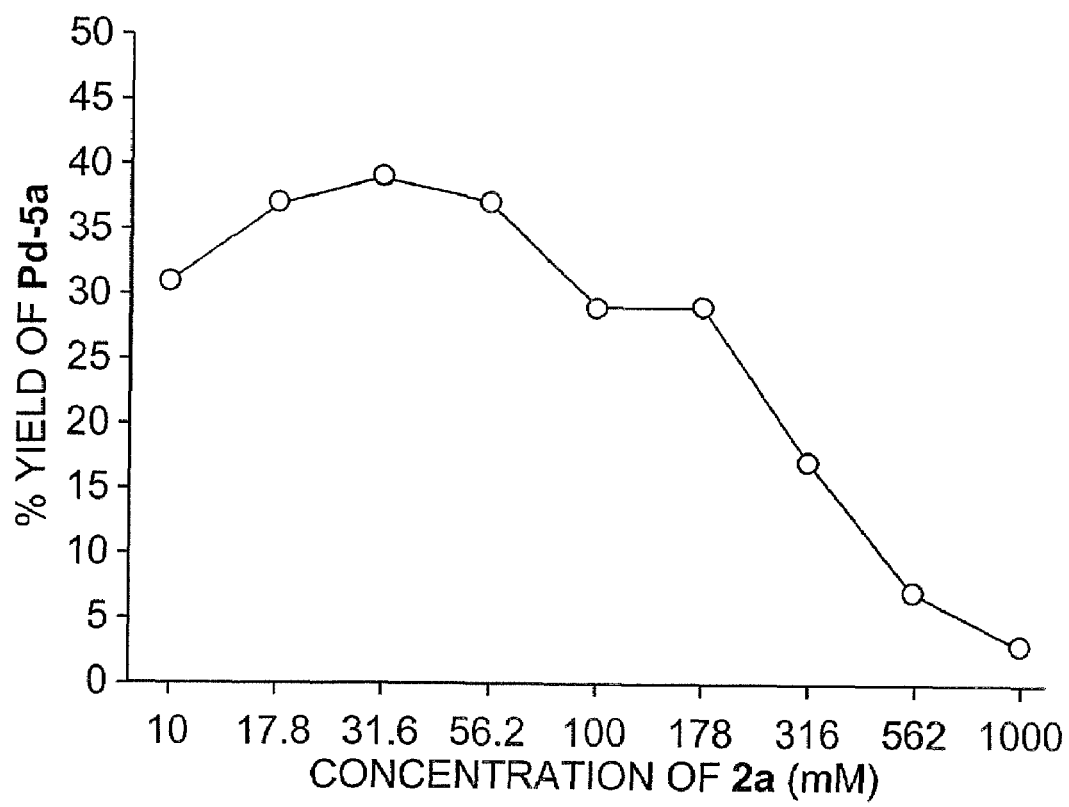

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

"Alkyl," as used herein, refers to a straight or branched chain hydrocarbon containing from 1 to 10 or 20 carbon atoms, or more. Representative examples of alkyl include, but are not limited to, methyl, ethyl, n-propyl, iso-propyl, n-butyl. sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like, which may be substituted or unsubstituted.

"Aryl," as used herein, refers to a monocyclic carbocyclic ring system or a bicyclic carbocyclic fused ring system having one or more aromatic rings. Representative examples of aryl include pyridyl, azulenyl, indanyl, indenyl, naphthyl, phenyl, tetrahydronaphthyl, and the like, which may in turn be substituted or unsubstituted.

"Acyl" is intended to mean a —C(O)—R group, where R is a suitable substituent such as H, alkyl or aryl, which may in turn be substituted or unsubstituted.

"Dipyrromethane" as used herein includes an unsubstituted or substituted dipyrromethane, which may be substituted one or more times at the 1, 2, 3, 5, 7, 8 or 9 positions with any suitable substituent such as halo, carbonyl, alkyl, fluoroalkyl including perfluoroalkyl, aryl (e.g., aryl at the 5 position; alkyl at the 1 and/or 9 position), fluoroaryl including perfluoroaryl, etc. Dipyrromethanes may be coupled to porphyrinic macrocycles at any suitable position on the dipyrromethanes, including the 1, 2, 3, 5, 7, 8, or 9 position.

"Dipyrrin" as used herein includes unsubstituted or substituted dipyrrin, which may be substituted one or more times at the 1, 2, 3, 5, 7, 8 or 9 positions with any suitable substituent such as halo, carbonyl, alkyl, fluoroalkyl including perfluoroalkyl, aryl (e.g., aryl at the 5 position; alkyl at the 1 and/or 9 position), fluoroaryl including perfluoroaryl, etc. Dipyrrins may be coupled to porphyrinic macrocycles at any suitable position on the dipyrrin, including the 1, 2, 3, 5, 7, 8, or 9 position.

"Dipyrromethane-1-carbinol" as described herein refers to the reduction product of a 1-acyldipyrromethane.

"Halo" as used herein refers to chloro, fluoro, bromo, or iodo.

All United States Patent references cited herein are to be incorporated by reference herein in their entirety.

Starting material 1-acyldipyrromethanes and 1-acyldipyrrins. Starting materials for the methods described herein are generally prepared by acylating a dipyrromethane. As such the starting materials are typically provided in a crude form or mixture combined with other reaction reagents and products. Depending upon the end use planned for the product, the dipyrromethane may be substituted at the 5 position with H, alkyl, or aryl; or in other embodiments may be substituted at the 5 position with a substituent such as a dipyrromethane, porphyrin, dipyrrin, or diacyldipyrromethane (which substituent may be directly coupled at the 5 position or coupled by an intermediate linking group such as an alkyl or aryl group). Acylation of the dipyrromethane may be carried out in any of a variety of ways. In one embodiment, acylating carried out by reacting the dipyrromethane with a compound of the formula RCOX, where R is an organic substituent such as alkyl or aryl and X is halo, to form a mixed reaction product comprising a 1-monoacyldipyrromethane or acylated at the 1 position with RCO—. In another embodiment, acylating is carried out by reacting the dipyrromethane with an acid chloride and a Grignard reagent to form the mixed reaction product comprising a 1-acyldipyrromethane. In another embodiment, acylating is carried out by reacting the dipyrromethane with an active ester to form the mixed reaction product comprising a 1-acyldipyrromethane. In another embodiment, acylating is carried out by reacting the dipyrromethane with a Vilsmeier reagent to form a mixed reaction product comprising a 1-acyldipyrromethane. See. e.g., D. Gryko et al., *J. Porphyrins Phthalocyanines* 7, 239-248 (2003). 1-acyldipyrrins are prepared by oxidation of the corresponding 1-acyldipyrromethane in accordance with known techniques.

Starting material 1,9-diacyldipyrromethanes and 1,9-diacyldipyrrins. 1,9-diacyldipyrromethanes are known and can be produced by a variety of techniques. The methods for diacylation of a dipyrromethane depend on whether the substituents at the 1- and 9-positions are the same or different. With identical substituents, the dipyrromethane can be treated with excess EtMgBr, generating the dipyrromethane analog of the "pyrrole Grignard reagent," followed by excess acid chloride. The reaction typically yields a mixture of the intermediate 1-acyldipyrromethane and the desired 1,9-diacyldipyrromethane. Diacyldipyrromethanes rarely crystallize well. Accordingly, the mixture is usually separated by chromatography, which can be tedious owing to the tending of the acyl-dipyrromethanes to streak on chromatographic media. With different substituents at the 1- and 9-positions, a stepwise synthesis is required. The first step entails reaction of the dipyrromethane with EtMgBr followed by a 2-S-pyridyl benzothioate, which exclusively and efficiently gives the monoacyldipyrromethane (2). P. Rao et al., *J. Org. Chem.* 2000, 65, 1084-1092. Reaction of the latter with EtMgBr followed by an acid chloride is employed to obtain the 1,9-diacyldipyrromethane (3). P. Rao et al., *J. Org. Chem.* 2000, 65, 7323-7344. Again, the diacyldipyrromethane is purified by chromatography. If acylated sequentially, the 1- and 9-substitutents ($R^2$) can be different. One convenient means for preparing the 1,9-diacyldipyrromethane starting materials is as described in copending application titled: J. Lindsey et al., Facile Synthesis of 1,9-Diacyldipyrromethanes; U.S. patent application Ser. No. 10/164,181, filed Sep. 3, 2003, the disclosure of which is incorporated by reference herein in its entirety. In general such methods involve making a metal complex, comprising the steps of: (a) acylating a dipyrromethane or a 1-acyldipyrromethane to form a mixed reaction product comprising a 1,9-diacyldipyrromethane; (b) combining said mixed reaction product with a compound of the formula $R_2MX_2$ in the presence of a base, where R is alkyl or aryl, M is Sn, Si, Ge, or Pb, and X is halo, OAc, acac or OTf, to form a metal complex of the formula $DMR_2$ in said mixed reaction product, wherein D is a 1,9-diacyldipyrromethane; and then (c) separating said metal complex from said mixed reaction product. The acylating step (a) may be carried out by: (i) reacting said dipyrromethane or 1-acyldipyrromethane with a compound of the formula $R^3COX$, where $R^3$ is alkyl or aryl and X is halo, to form said mixed reaction product comprising a 1,9-diacyldipyrromethane acylated at the 1 and 9 positions with $R^3CO$—; (ii) reacting said dipyrromethane or 1-acyldipyrromethane with an acid chloride and a Grignard reagent to form said mixed reaction product comprising a 1,9-diacyldipyrromethane; (iii) reacting said dipyrromethane or 1-acyldipyrromethane with an active ester to form said mixed reaction product comprising a 1,9-diacyldipyrromethane; or (iv) reacting the dipyrromethane or 1-acyldipyrromethane with a Vilsmeier reagent to form the mixed reaction product comprising a 1,9-diacyldipyrromethane. The base may be triethylamine, tributylamine, N,N-diisopropylamine, DBU, DBN, or 2,6,-di-tert-butylpyridine. M may be Sn. The compound of the formula $R_2MX_2$ may be immobilized on a solid support. The method preferably further comprises the step of: (d) treating said metal complex with an acid (e.g., trifluoroacetic acid, trichloroacetic acid, acetic acid, HCl, p-toluene sulfonic acid) to produce a 1,9-diacyldipyrromethane. 1,9-diacyldipyrrins are the oxidized analogs of the corresponding 1,9-diacyldipyrromethane and are prepared in accordance with known techniques (see, e.g., Tamaru, S.-I.; Yu, L.; Youngblood, W. J.; Muthukumaran, K.; Taniguchi, M.; Lindsey, J. S. *J. Org. Chem.* 2004, 69, 765-777).

Reagents and reactions. As noted above, methods of the invention involve either (i) condensing a 1-acyldipyrromethane, 1-acyldipyrrin, or a dipyrromethane-1-carbinol with itself in a reaction mixture comprising an organic solvent and a reagent comprising metal M to form an intermediate; or (ii) condensing a 1,9-diacyldipyrromethane or a 1,9-diacyldipyrrin with a dipyrromethane in a reaction mixture comprising an organic solvent and a reagent to produce a porphyrin having said metal M complexed therewith. The metal M is donated by the second reagent, which is a palladium or copper complex.

Copper complexes used to carry out the present invention are, in general, copper 0, copper I, copper II, or copper III complexes. Such complexes are well known in the art, with examples including but not limited to CuCl, $CuCl_2$, $Cu(OAc)_2$ and $Cu(OH)_2$.

Palladium complexes used to carry out the present invention are, in general, palladium 0, palladium II, or palladium IV complexes, with palladium II and palladium IV complexes preferred. Such complexes are generally described as compounds of the formulas (in the case of Pd(II)) $PdX_2$, $PdX_2L_2$, $PdX_2L_4$, or (in the case of Pd(IV)) $PdX_4Y_2Z_2$, wherein X is an anion, L is a neutral group; Y is a cation, and Z is an anion. Such complexes are well known in the art.

Specific examples of Pd(IV) complexes that may be used as reagents in the present invention are: $K_2PdCl_6$, $Na_2PdCl_6$, and $(NH_4)_2PdCl_6$.

Specific examples of Pd(II) complexes that may be used as reagents in the present invention are: $Pd(OAc)_2$, $Pd(acac)_2$, $PdCl_2$, $PdBr_2$, $Pd(CN)_2$, $PdI_2$, PdO, $PdO.xH_2O$, PdS, $Pd(O_2CCF_3)_2$, $C_3H_5PdCl_2$, $(NH_4)_2PdCl_4$, $Pd(NO_3)_2 \cdot xH_2O$, $PdSO_4.H_2O$, $K_2PdBr_4$, $K_2PdCl_4$, $Na_2PdCl_4$, $K_2Pd(S_2O_3)_2(CH_2O)$, $(CH_3CO_2)_2Pd[P(C_6H_5)_3]_2$, $Pd(NH_3)_2(NO_2)_2$, $Pd(NH_3)_2(NO_3)_2$, $[Pd(NH_3)_4][PdCl_4]$, $Pd(NH_3)_2Cl_2$, $PdCl_2(CH_3CN)_2$, $PdCl_2[P(C_6H_5)_3]_2$, $PdCl_2(C_6H_5CN)_2$, $Pd(O_2CC_2H_5)_2$, $PdCl_2[P(C_6H_{11})_3]_2$, $PdCl_2[P(C_6H_5)_3]_2$, $PdCl_2[P(CH_3C_6H_5)_3]_2$, $Pd(BF_4)_2(CH_3CN)_4$, trans-di(μ-acetato)bis[o-(di-o-tolyl-phosphino)benzyl]dipalladium, dichloro(1,2-bis(diphenylphosphino)ethane)palladium(II), dichloro[1,1'-bis(diphenylphosphino)ferrocene]palladium(II) dichloromethane adduct, palladium(II)hexafluoroacetylacetonate, dichloro(1,5-cyclooctadiene)palladium(II), ammonium bis(oxalato)palladium(II), dichloro(ethylenediamine)palladium(II), bis(pyridine)palladium(II) chloride, chloro(di-2-norbornylphosphino)(2-dimethylaminomethylferrocen-1-yl)palladium(II), chloro(di-2-norbornylphosphino)(2'-dimethylamino-1,1'-biphenyl-2-yl)palladium(II), dichloro(1,3-bis(diphenylphosphino)propane)palladium(II), bis [tris(4-(1H, 1H,2H,2H-perfluorodecyl)pheny)phosphine]palladium(II)dichloride, benzylbis(triphenyl phosphine)palladium(II) chloride, (bicyclo[2.2.1]hepta-2,5-diene)dichloropalladium(II), ([2S,3S]-bis[diphenylphosphino]butane)(eta$^3$-allyl)palladium(II) perchlorate, acetato(2'-di-t-butylphosphino-1,1'-biphenyl-2-yl)palladium(II), and allylchloro[1,3-bis(2,6-diisopropylphenyl)imidazol-2-ylidene]palladium(II).

Any suitable solvent can be used, including but not limited to alcohol solvents, ethereal solvents, water, tetrahydrofuran, and mixtures thereof. Ethanol is currently preferred. Preferably the reaction mixture further includes a base (e.g., KOH or NaH). The reaction mixture preferably has a pH of at least 7, and preferably comprises not more than 0.5, 0.2, 0.1, or even 0.05 percent by weight added acid. Time and temperature are not critical and the condensing step may, for example, be carried out at a temperature of 0 to 150° C. for a time of 1 or 2 minutes to 1 hour or 24 hours or more. Any suitable oxidizing agent may be used, with ambient oxygen being particularly convenient.

The porphyrin compound can be left complexed with the metal or the metal displaced with an acid in accordance with known techniques.

Utility. The porphyrinic macrocycles produced by the methods described herein are useful, among other things, for the production of polymers thereof which may be immobilized or coupled to a substrate and used as light harvesting rods, light harvesting arrays, and solar cells, as described for example in U.S. Pat. No. 6,407,330 to Lindsey et al. or U.S. Pat. No. 6,420,648 to Lindsey. Porphyrinic macrocycles are also useful immobilized to a substrate for making charge storage molecules and information storage devices containing the same. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al. The porphyrinic macrocycle may comprise a member of a sandwich coordination compound in the information storage molecule, such as described in U.S. Pat. No. 6,212,093 to Li et al. or U.S. Pat. No. 6,451,942 to Li et al.

The porphyrinic macrocycles containing palladium produced by the methods described herein are useful as phosphorescent sensors in medical diagnostic and industrial applications, for example by inclusion in a paint that can be applied to an airfoil surface to examine air flow across that surface with an optical device (the paint responding to differences in air pressure and hence oxygen concentration by varying intensity of phosphorescence).

The present invention is explained in greater detail in the following non-limiting Examples.

Experimental

We herein describe the results of the screen of a wide variety of metal reagents with 1-acyldipyrromethanes. We then focus on palladium and copper reagents and explore the scope of 1-acyldipyrromethanes that yield the trans-$A_2B_2$-porphyrin. The best conditions are applied to the reaction of a 1,9-diacyldipyrromethane+a dipyrromethane to give the corresponding porphyrin. The reactants thus include dipyrromethane 1,[14] 1-acyldipyrromethane 2,[7,15] and 1,9-diacyldipyrromethane 3[16] species (Chart 1). These studies are complemented by an examination of optimal conditions for forming palladium porphyrins from the corresponding free base porphyrins. Taken together, this work provides new routes to palladium porphyrins. More broadly, this work identifies a new pathway to porphyrins that employs less reduced species (acyldipyrromethanes rather than reduced, dipyrromethane-carbinols), employs basic conditions, does not require the use of a quinone oxidant, and likely exploits metal templation during macrocycle formation.

Results and Discussion

1. Survey of 1-Acyldipyrromethane-Metal Complexes. A variety of metal reagents were examined as potential complexation aids for isolation of 1-acyldipyrromethanes. We used 1-(p-toluoyl)-5-phenyldipyrromethane (2a) as a substrate with various metal reagents. The metals examined include $Mg(OAc)_2.4H_2O$, $Sc(OTf)_3$, $TiF_4$, $MnCl_2$, $Mn(OAc)_2$, $FeBr_3$, $Fe(OAc)_3$, $Fe(acac)_3$, $Co(OAc)_2.4H_2O$, $Ni(OAc)_2.4H_2O$, $Cu(OAc)_2.H_2O$, $Zn(OAc)_2.2H_2O$, $GeI_4$, $MoCl_3$, $RuCl3.H_2O$, $Pd(OAc)_2$, AgOTf, $CdCl_2$, $InCl_3$, $In(OAc)_3$, $SnF_4$, $SbCl_5$, $TeCl_4$, $CeI_3$, $EuCl_3$, $Dy(OTf)_3$, $Yb(OTf)_3$, $Pt(C_6H_5CN)_2Cl_2$, TlOAc, and $BiCl_3$. A mixture of 2a (42 mM) and KOH (420 mM) in EtOH was treated with one of the various metal reagents at reflux for 1 h. (Note that our prior study to identify complexation aids for 1-acyldipyrromethanes employed reaction in the absence of base at room temperature.[7]) Most of the metal reagents examined gave no reaction or formed multiple components. A readily isolable complex was obtained only with $Cu(OAc)_2.H_2O$ or $Pd(OAc)_2$ under the conditions that were investigated.

The anticipated product in the reaction of 2a (42 mM) and KOH (420 mM) with $Cu(OAc)_2.H_2O$ (21 mM) in EtOH at reflux for 1 h was the corresponding dipyrromethane complex (Scheme 1). TLC examination showed complete consumption of 2a and the appearance of a non-polar spot as well as black material at the origin. The UV-vis spectrum of the crude mixture showed a weak absorption at 413 nm, attributed to a trace amount of copper porphyrin, and a strong absorption at 480 nm. The major product obtained by chromatographic purification was a red solid, which exhibited an absorption peak at 480 nm and m/z=740, consistent with the copper complex of the 1-acyldipyrrin Cu-4a rather than the 1-acyldipyrromethane. Treatment of Cu-4a in CH$_2$Cl$_2$ with dithiothreitol (DTT), a reagent known to cause disassembly of bis(dipyrrinato)copper complexes,[17] afforded the free-base 1-acyldipyrrin 4a with characteristic absorption at 430 nm. The yield of Cu-4a was 37% in the reaction of 2a and Cu(OAc)$_2$·2H$_2$O.
Chart 1
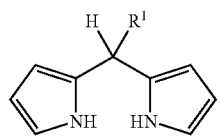
1
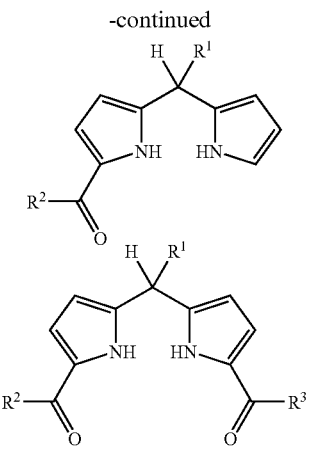
2
3
Scheme 1
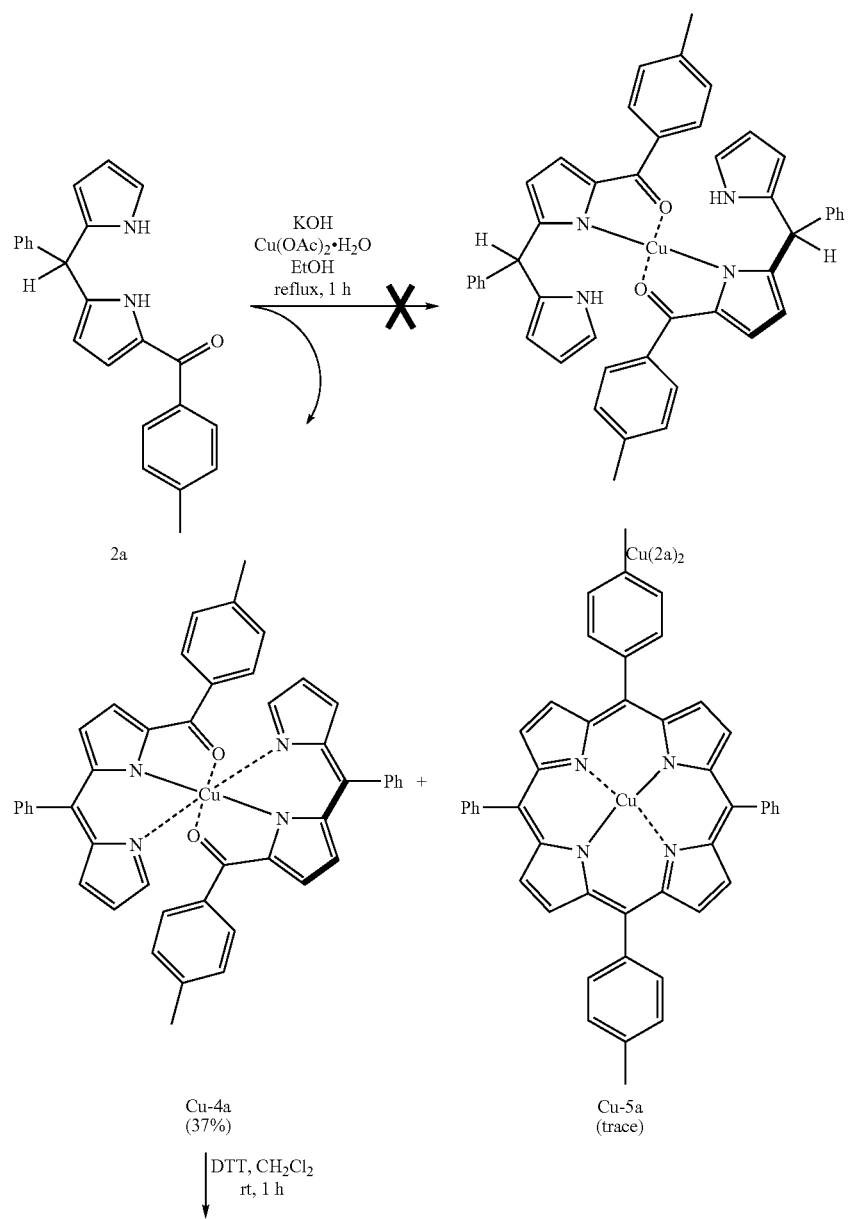

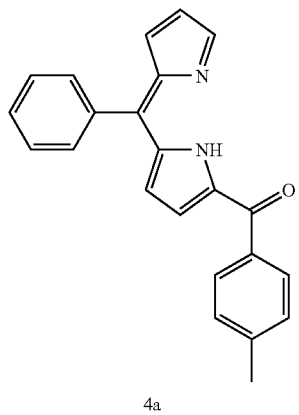

4a

The formation of a trace amount of copper-porphyrin in the reaction of 2a with KOH and Cu(OAc)$_2$·H$_2$O prompted examination of the same reaction under more forcing conditions. Accordingly, a solution of 2a (83 mM) and KOH (830 mM) in ethylene glycol was treated with Cu(OAc)$_2$·H$_2$O at reflux for 18 h under an atmosphere of air. The corresponding porphyrin Cu-5a was isolated upon chromatography in 13% yield.

The reaction of 2a with Pd(OAc)$_2$ in refluxing ethanol containing KOH exposed to air afforded the corresponding palladium porphyrin Pd-5a in 42% yield (Scheme 2). The formation of the Pd-porphyrin was confirmed by $^1$H NMR spectroscopy, LD-MS analysis, and the characteristic visible absorption bands at 418 and 524 nm. No other porphyrin species were observed by LD-MS and TLC analysis.

Scheme 2

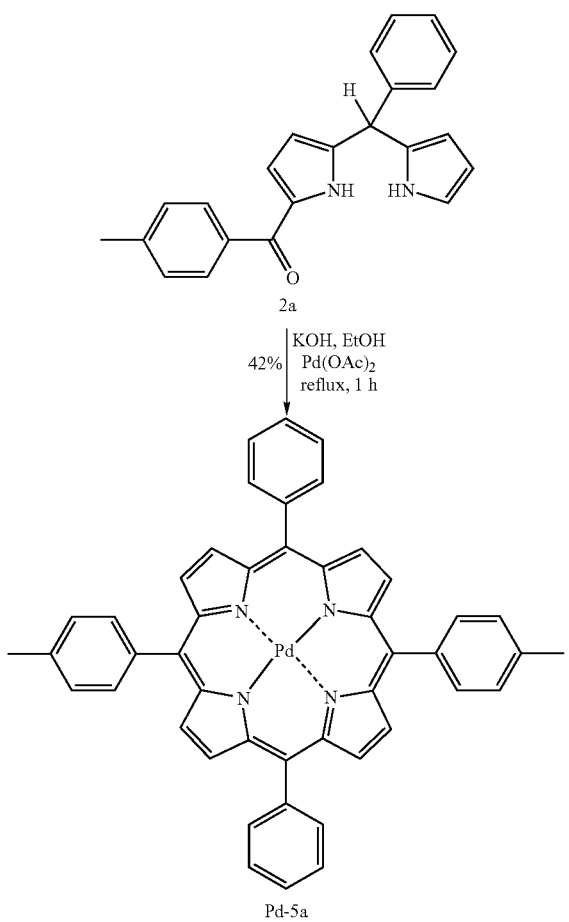

2. Optimization of Reaction Conditions for Palladium-Porphyrin Formation.

A. Reagents. The self-condensation of 2a in the presence of Pd(OAc)$_2$ and KOH in ethanol to give palladium porphyrin Pd-5a prompted a broader survey of the conditions that would provide access to palladium porphyrins. The survey encompassed the nature of the palladium reagent, the nature of the base, and the absolute requirement for various components. The results are listed in Table 1.

TABLE 1

Survey of Conditions for the Self-Condensation of 2a.[a]

| Entry | Variation from the standard conditions | Yield of Pd-5a[b] |
|---|---|---|
| 1 | None | 33% |
| 2 | Pd(acac)$_2$ in place of Pd(OAc)$_2$ | 33% |
| 3 | Pd(CH$_3$CN)$_2$Cl$_2$ in place of Pd(OAc)$_2$ | 41% |
| 4 | PdBr$_2$ in place of Pd(OAc)$_2$ | 3% |
| 5 | PdCl$_2$ in place of Pd(OAc)$_2$ | 3% |
| 6 | omission of Pd(OAc)$_2$ | 0%[c] |
| 7 | omission of KOH | 0% |
| 8 | omission of Pd(OAc)$_2$, 1-pentanol in the place of EtOH at reflux for 18 h | 0%[c] |
| 9 | TEA/THF, NaH/THF, pyridine/toluene[d] or NaOAc/DMSO[d] in place of KOH/EtOH | 0% |
| 10 | TEA/DME or NaOAc/DMSO in place of KOH/EtOH | 1-2%[e] |
| 11 | NaOMe/THF in place of KOH/EtOH, under Ar | 0% |
| 12 | DBU or K$_2$CO$_3$ in place of KOH | <8% |
| 13 | Ba(OH)$_2$·8H$_2$O in place of KOH | 33% |
| 14 | Reaction at room temperature | 29% (18 h) |

[a]The standard conditions entail use of 2a (0.125 mmol, 40 mM), KOH (1.25 mmol), and Pd(OAc)$_2$ (0.063 mmol) in ethanol at reflux for 1 h.
[b]The yield of porphyrin Pd-5a was determined spectroscopically.
[c]No free base porphyrin observed.
[d]The standard conditions entail use of 2a (0.10 mmol, 100 mM), base (0.50 mmol), Pd(OAc)$_2$ (0.06 mmol) and bubbling oxygen at 75° C. for 1 h.
[e]The standard conditions entail use of 2a (0.10 mmol, 100 mM), base (0.50 mmol) and Pd(OAc)$_2$ (0.06 mmol) at 65° C. for 1 h.

Among several palladium reagents, Pd(CH$_3$CN)$_2$Cl$_2$ afforded the highest yield (entries 1-5). The omission of palladium reagent or KOH resulted in no porphyrin (entries 6, 7). The omission of the palladium reagent while carrying out the reaction in refluxing 1-pentanol gave no free base porphyrin even after 18 h (entry 8). The reaction was quite sensitive to the nature of the base, with poor results obtained with TEA, NaH, DBU, K$_2$CO$_3$ (entries 9-12), though Ba(OH)$_2$·8H$_2$O gave porphyrin in yield comparable with that of the KOH reaction (entry 13). The reaction at room temperature succeeded but was quite slow (entry 14). The effect on the yield of palladium porphyrin with number of equivalents of KOH (1, 2, 5, or 10 equivalents) was studied. The best result was obtained with 5 or 10 equivalents of KOH with respect to 1-acyldipyrromethane 2a.

B. Effects of Concentration. The effect of concentration was examined by performing the reaction of 2a at concentrations ranging from 10 mM to 1 M, with Pd(CH$_3$CN)$_2$Cl$_2$ and KOH in EtOH at reflux for 1 h. Note that we use the term concentration to facilitate comparison even though the reaction mixtures may be heterogeneous. The concentrations of KOH and Pd(CH$_3$CN)$_2$Cl$_2$ were altered as required to maintain fixed ratios with respect to the concentration of 2a. The best results (~30%) were obtained when the reaction was performed between 10-178 mM concentrations (FIG. 1A). The reactions conducted at concentration higher than 178 mM showed a gradual decrease in the yield of palladium-porphyrin.

Figure 1B:
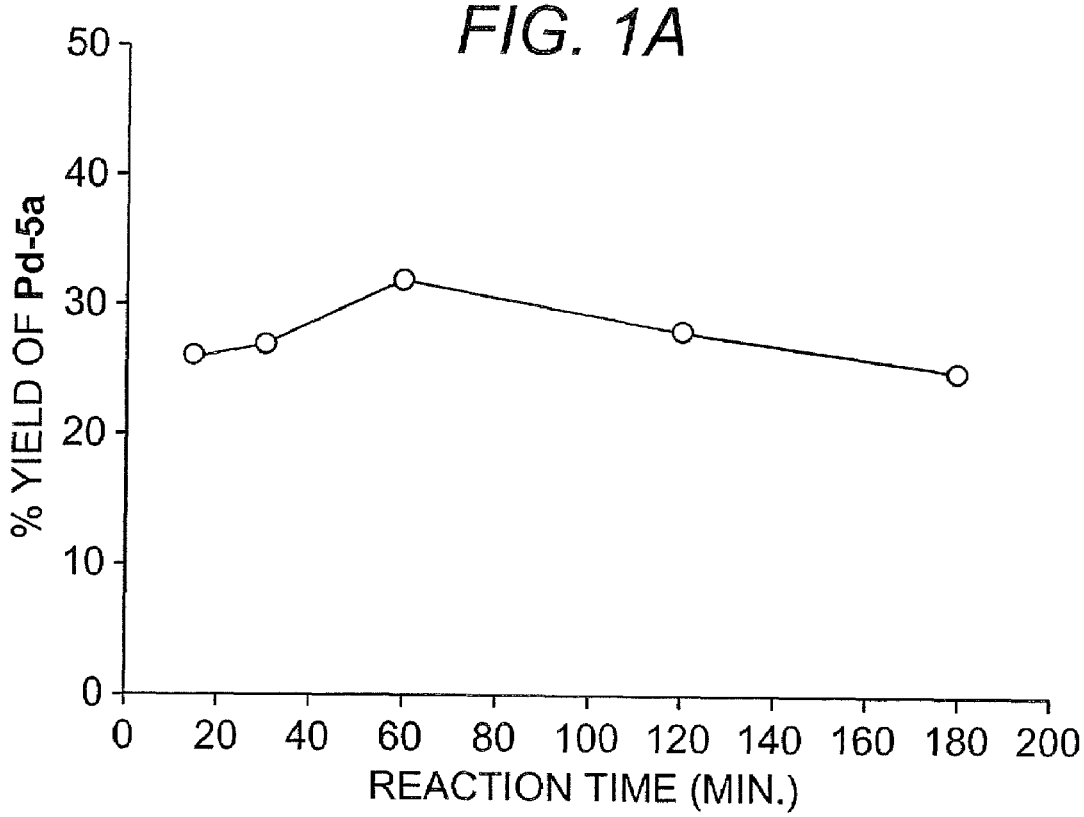
FIG. 1B. The time course for the self-condensation yielding the palladium porphyrin. The reaction of 1-acyldipyrromethane 2a (100 mM) was carried out in refluxing ethanol exposed to air with KOH (500 mM) and Pd(CH$_3$CN)$_2$Cl$_2$ (60 mM).

C. Time Course. The formation of palladium porphyrin using 1-acyldipyrromethane (2a) (100 mM), KOH (500 mM) and Pd(CH$_3$CN)$_2$Cl$_2$ (60 mM) in EtOH at reflux was examined at various time points (15 min to 3 h). The maximum yield of porphyrin (~32%) was obtained within 60 min (FIG. 1B). The yield of porphyrin after 1 h showed no significant change.

D. Effect of Pd Oxidation State. We examined the effect of different oxidation states of palladium including Pd(0) and Pd(IV) on the palladium porphyrin formation under basic conditions. Reactions were performed under anaerobic conditions using freeze-pump-thaw degassed ethanol, which was added to a degassed mixture of solid reagents. The resulting mixture was heated at 70° C. for 1 h while stirring. The Pd(0) and Pd(IV) oxidation states were achieved with Pd(PPh$_3$)$_4$ and Na$_2$PdCl$_6$, respectively. Reactions were monitored over time, and the yields observed at 1 h are shown in Table 2. In the case of Pd(0), there was no porphyrin formation under anaerobic conditions even with DDQ oxidation, or under aerobic conditions. With Pd(IV), the porphyrin was obtained in 7% yield under anaerobic conditions but 35% yield under aerobic conditions. The results of the reactions with Pd(II) and Pd(IV) are quite similar under aerobic conditions.

TABLE 2

Effect of Pd Oxidation State on Porphyrin Formation.[a]

| Reaction Conditions | Porphyrin Yields (%)[b] | | |
|---|---|---|---|
| | Pd(PPh$_3$)$_4$ | Pd(CH$_3$CN)$_2$Cl$_2$ | Na$_2$PdCl$_6$ |
| Anaerobic | 0 | 19 | 7 |
| Anaerobic + DDQ[c] | 0 | 16 | 7 |
| Aerobic | 0 | 29 | 23 |

[a]Reaction of 2a (100 mM) in ethanol containing the palladium reagent (60 mM) and KOH (500 mM) was performed for 1 h at 70° C. under the specified conditions, affording porphyrin Pd-5a.
[b]Yields were determined spectroscopically.
[c]Reaction was performed under anaerobic conditions; samples were removed and treated with DDQ prior to yield determination via spectroscopy.

In summary, best conditions for porphyrin formation from 1-acyldipyrromethane (2a) are achieved with a modest concentration of 2a (31.6 mM) and corresponding concentration of ethanolic KOH (158 mM) and Pd(CH$_3$CN)$_2$Cl$_2$ (18.9 mM) at reflux for 1 h. These conditions were identified by studies that employed yield determination via spectroscopic monitoring of the reactions. For scale-up purposes, the reaction was done using a slightly higher concentration of 2a (100 mM). Thus, the reaction of 2a (100 mM), KOH (500 mM) and Pd(CH$_3$CN)$_2$Cl$_2$ (60 mM) in EtOH at reflux for 1 h gave the palladium-porphyrin Pd-5a as a purple crystalline solid in 53% isolated yield. No other porphyrin species were observed upon LD-MS analysis of the crude reaction mixture.

3. Scope. A. Acyldipyrromethane Substituents. Exploration of the generality of the palladium-porphyrin forming conditions required access to a set of 1-acyldipyrromethanes bearing a variety of substituents at the 1- and 5-positions. The general method for synthesis of 1-acyldipyrromethanes entails treatment of a dipyrromethane with EtMgBr at −78° C. in THF followed by addition of a S-2-pyridylthioate[18] (Mukaiyama reagent).[15] A set of Mukaiyama reagents includes four known compounds (6a-d, acyl substituents=p-tolyl, p-anisyl, pentafluorophenyl, and pentyl, respectively).[7,16] The reaction of acid chloride and 2-pyridylthiol following a refined procedure[16] afforded Mukaiyama reagents 6e and 6g (Scheme 3). The synthesis of a Mukaiyama reagent bearing a $^{13}$C-labeled acyl unit (6f) was achieved by reaction of $^{13}$C-1-benzoic acid with 2-pyridyl disulfide and triphenylphosphine following a known procedure (references 18 and 19).

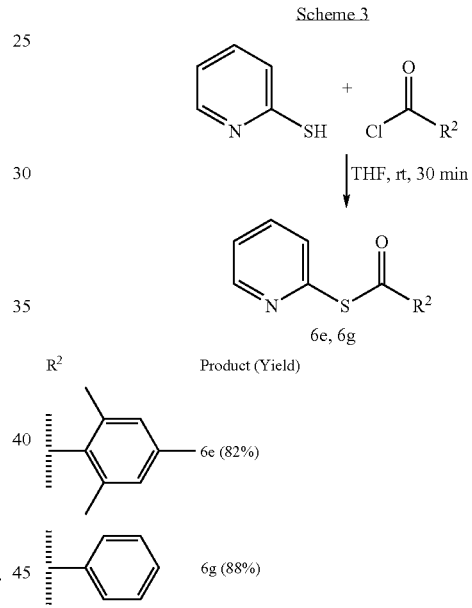

Scheme 3

The 1-acyldipyrromethanes were prepared by reaction of the dipyrromethanes 1a-c and the desired Mukaiyama reagents 6a-f using a literature procedure[15] (Scheme 4). To facilitate purification of the 1-acyldipyrromethanes, we recently developed a boron-complexation strategy[7] wherein the crude acylation mixture is treated with a dialkylboron triflate and TEA, affording the hydrophobic dialkylboron complex of the 1-acyldipyrromethane. The complex can be readily isolated by precipitation/crystallization with limited or no chromatography. Application of the boron-complexation strategy afforded the 1-acyldipyrromethane-dialkylboron complexes 2a-d and 2f,g. A dialkylboron complex was not attempted for the 1-acyldipyrromethanes 2e and 2h, which were prepared following a known procedure.[15,19] The 1-acyldipyrromethane-dialkylboron complexes were decomplexed by treatment with 1-pentanol in refluxing THF, affording the desired 1-acyldipyrromethanes. The 1-formyl-dipyrromethane 2i was prepared following a known procedure.[20]

SCHEME 4
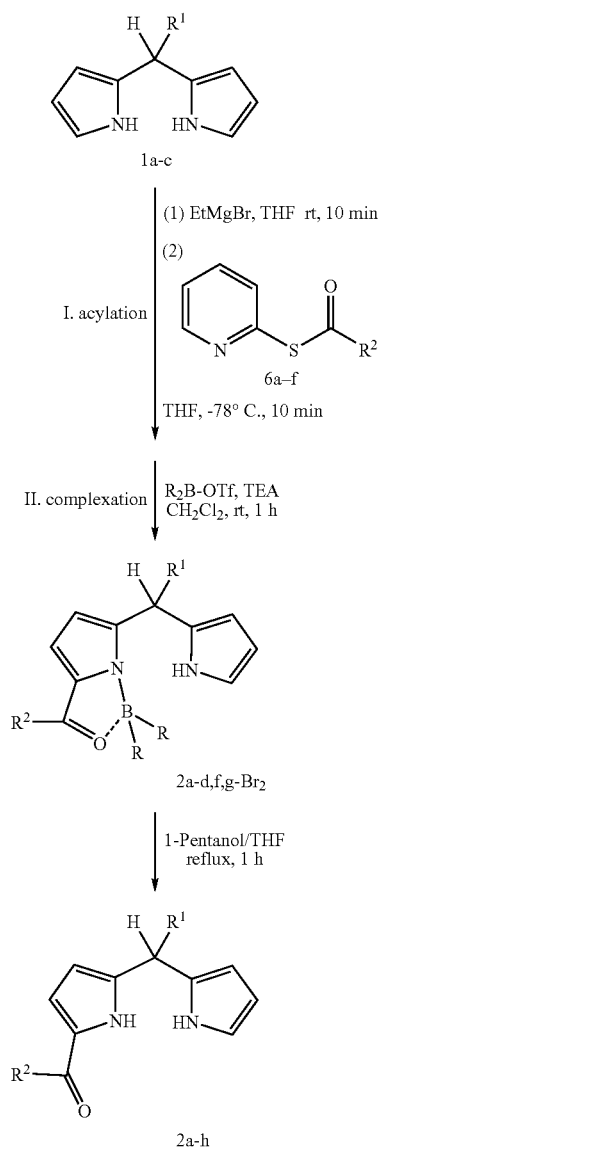

SCHEME 4-continued

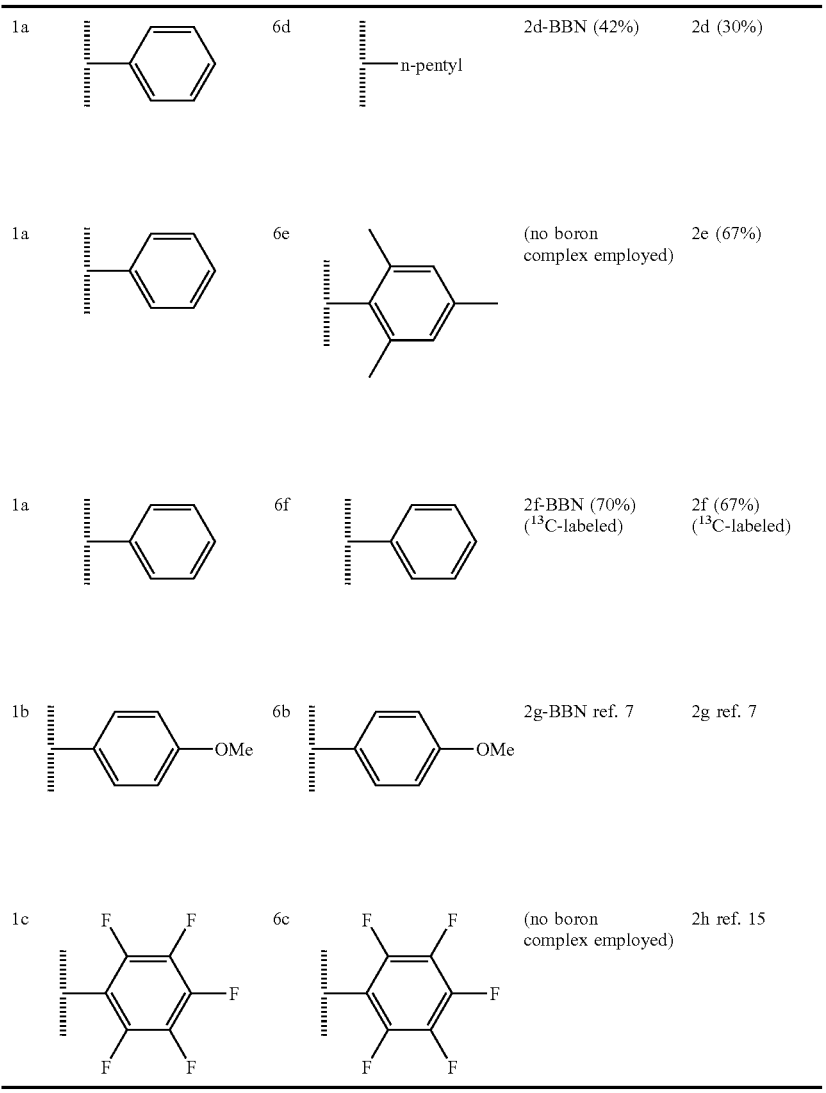

To gain insight into the process of porphyrin formation from the 1-acyldipyrromethane, we sought to probe complexation and/or reduction processes that might occur at the α-acyl position of the dipyrromethane. For this, we chose to synthesize $^{13}$C-labeled reagents necessary for the synthesis of the $^{13}$C—Pd-porphyrin: $^{13}$C—S-2-pyridyl benzothioate (6f), $^{13}$C-1-benzoyl-5-phenyldipyrromethane, $^{13}$C-5-phenyl-dipyrromethanemonocarbinol (2f-OH) (which is a possible intermediate) and to monitor the reaction at various temperatures in NMR spectroscopy in an effort to observe changes in the chemical shift of the carbonyl group during the reaction. The isotopically labeled Mukaiyama reagent $^{13}$C—S-2-pyridyl benzothioate (6f) was employed to form the desired $^{13}$C-labeled 1-acyldipyrromethane 2f, and the latter was reduced with NaBH$_4$ to give the $^{13}$C-labeled monocarbinol 2f-OH.

The generality of the palladium-porphyrin forming conditions were examined with 1-acyldipyrromethanes (2b-e,g-i) bearing various substituents at the 1- and 5-positions (Scheme 5). Self-condensation of 1-acyldipyrromethanes with the electron-releasing substituents at the 1- and 5-positions resulted in porphyrins with higher yields than with the electron-withdrawing substituents. Examination of a substrate with the pentafluorobenzoyl group in the 1-position led to a porphyrin containing two ethoxy substituents in place of fluoro atoms. On the basis of the well-documented susceptibility of the para position of pentafluorophenyl groups to nucleophilic substitution,[21,22] the product is proposed as porphyrin Pd-5c. With the mesitoyl group in the 1-position of the dipyrromethane, no palladium-porphyrin was observed. The addition of DDQ also gave no porphyrin, thereby suggesting that the failure of the reaction lies in the condensation rather than in any oxidation processes. The reaction in 1-pentanol (bp 136-138° C.) instead of ethanol (bp 78° C.) again showed no palladium-porphyrin formation even after 18 h. In the case of 2h, which contains pentafluorophenyl substituents in both the 1-acyl and 5-positions, the yield of palladium porphyrin was ~1.4%. No significant change was observed upon adding DDQ or by performing the reaction in refluxing 1-pentanol in place of ethanol for 18 h. Other than two failures, yields were 29-57%.

SCHEME 5
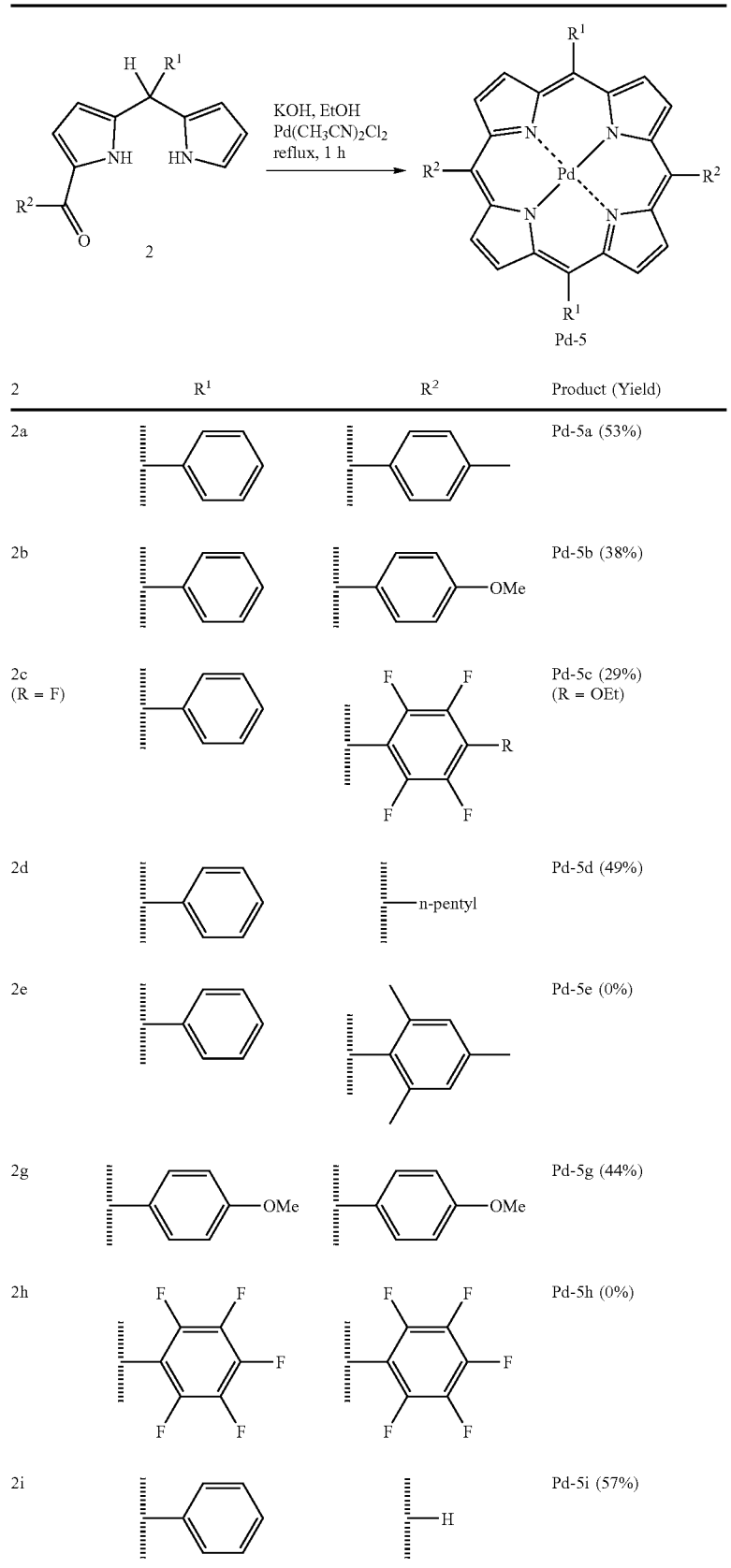

B. Reactivity of Distinct Substrates. A variety of substrates related to 1-acyldipyrromethanes were examined under the standard reaction conditions, using Pd(CH$_3$CN)$_2$Cl$_2$ and KOH in refluxing ethanol exposed to air. In general, the acylpyrrolic species was employed at 100 mM with the same ratio of reagents as employed above. The results are shown in Table 3.

TABLE 3

Reactivity of Distinct Substrates.

| Entry | Reactants | Conditions[a] | Expected product | Yield[b] |
|---|---|---|---|---|
| 1 | 2a-OH | 1 h | Pd-5a | 13% |
| 2 | 4a | 24 h | Pd-5a | 14% |
| 3 | 7 | 24 h[c] | PdTPP | 0% |
| 4 | 1a + benzaldehyde | 6 h[d] | PdTPP | 5% |
| 5 | pyrrole + benzaldehyde | 3 h[e] | PdTPP | 0% |

[a]The reactions were performed in ethanol containing KOH and Pd(CH$_3$CN)$_2$Cl$_2$ at reflux exposed to air for the specified time. The standard concentrations were as follows unless noted otherwise: reactant (100 mM), KOH (500 mM), and Pd(CH$_3$CN)$_2$Cl$_2$ (60 mM).
[b]The yield of the product was determined spectroscopically.
[c]The reaction employed Pd(CH$_3$CN)$_2$Cl$_2$ at 30 mM.
[d]The reaction employed both 1a and benzaldehyde at 100 mM.
[e]The reaction employed pyrrole (400 mM), benzaldehyde (400 mM), KOH (1 M) and Pd(CH$_3$CN)$_2$Cl$_2$ (100 mM).

The self-condensation of the dipyrromethane-monocarbinol 2a-OH gave the metalloporphyrin but the yield was substantially lower (13%) than for reaction with the 1-acyl-dipyrromethane 2a (53%) (entry 1). The self-condensation of 1-acyldipyrrin 4a gave Pd-porphyrin in 14% yield (entry 2). The 1-acyldipyrrin 4a was prepared in 68% yield by the oxidation of 1-acyldipyrromethane 2a with DDQ. The self-condensation of 7 at reflux for 24 h did not give any of the corresponding $A_4$-porphyrin (entry 3). The condensation of 5-phenyldipyrromethane 1a with benzaldehyde gave the Pd-porphyrin in 5% yield (entry 4). However, the very similar condensation of pyrrole (400 mM) with benzaldehyde (400 mM) in the presence of $Pd(CH_3CN)_2Cl_2$ (100 mM) and KOH (1 M) in EtOH at reflux for 3 h gave no porphyrin (entry 5).

Other routes wherein the substrates contain an α-acylpyrrole motif also were examined. The condensation of 1,9-diacyldipyrromethane 3a with 1a under the standard Pd-porphyrin forming conditions gave palladium porphyrin Pd-5a in 25% yield (Scheme 6). The survey of other (non-Pd or Cu) metal reagents (as examined for 1-acyldipyrromethane) in the condensation of 1,9-diacyldipyrromethane 3a and dipyrromethane 1a resulted in no porphyrin except in the case of $Pd(OAc)_2$ affording Pd-5a (13% yield) with characteristic absorption bands at 418 and 524 nm.

One experiment was performed to use the 1-acyldipyrromethane-$BR_2$ complex (2a-BBN) directly in forming the Pd-porphyrin, thereby avoiding the requirement for decomplexation of the 9-BBN group. A suspension of 2a-BBN (100 mM) and KOH (500 mM) in EtOH was refluxed for 1 h. Then, the mixture was treated with $Pd(CH_3CN)_2Cl_2$ (60 mM) at reflux for 1 h. UV-vis spectroscopic analysis indicated a 13% yield of Pd-porphyrin formation.

Attempts to use $Ni(OAc)_2 \cdot 4H_2O$ or $Pt(C_6H_5CN)_2Cl_2$ in the self-condensation of 2a under the optimized palladium-porphyrin forming conditions using refluxing 1-pentanol in the place of ethanol indicated ~0.5-1% metal-porphyrin formation by UV-vis analysis.

4. Mechanistic Considerations. It is noteworthy that the porphyrin is formed directly from the 1-acyldipyrromethane (2) without apparent conversion to the carbinol and without any added oxidizing agent (such as DDQ or p-chloranil). Moreover, the reaction uses basic conditions unlike the self-condensation of dipyrromethane-monocarbinols where acidic conditions are employed. Given that the palladium porphyrin is formed directly from 1-acyldipyrromethane (2), these conditions supercede the reaction steps typically employed in the synthesis of palladium porphyrins: (1) reduction of the 1-acyldipyrromethane; (2) acid-catalyzed condensation; (3) oxidation of the porphyrinogen intermediate; and (4) metal insertion. Thus, the synthesis of the

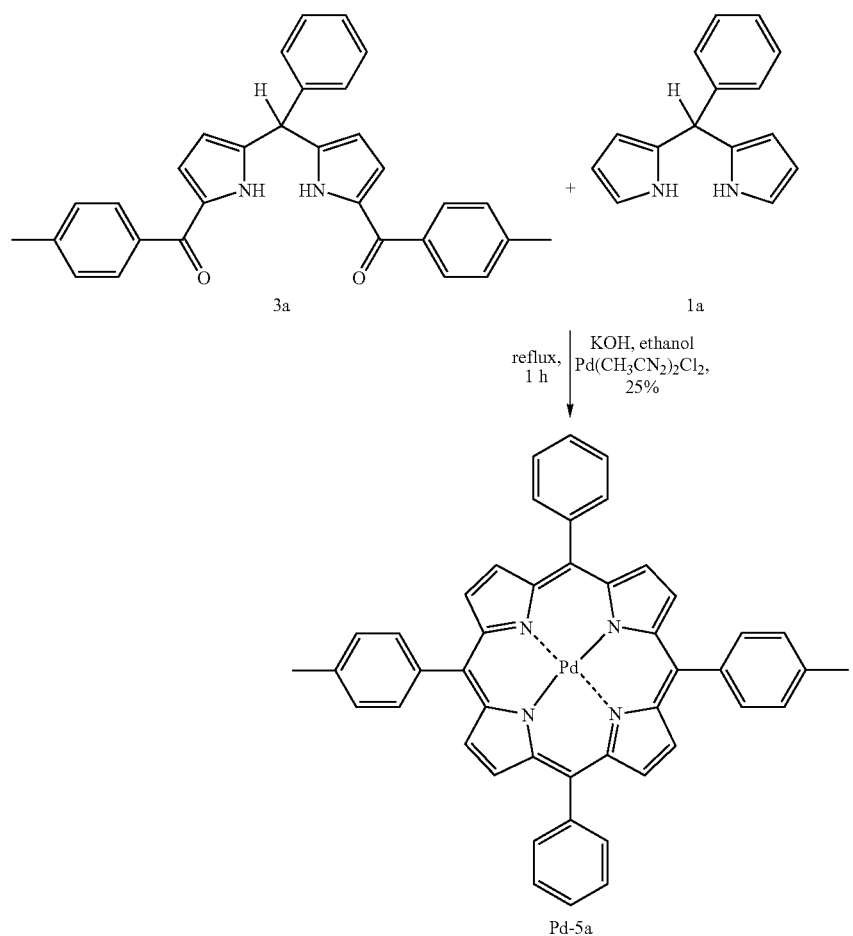

Scheme 6 palladium-porphyrin directly from self-condensation of 1-acyldipyrromethane or condensation of a 1,9-diacyldipyrromethane with a dipyrromethane occurs in a single-flask process whereas the previous synthesis involved four distinct steps (reduction, acid-catalyzed condensation, oxidation, and palladium insertion). The previous synthesis involved a 2×(2e$^-$+2H$^+$) reduction followed by a 6e$^-$+6H$^+$ oxidation whereas the new synthesis involves only a 2e$^-$+2H$^+$ oxidation overall (per two 1-acyldipyrromethanes). The current reaction scheme assumes that molecular oxygen serves as 2e$^-$+2H$^+$ acceptor. Therefore, self-condensation of 1 mmol of 1-acyldipyrromethane (2) will stoichiometrically require 0.25 mmol of O$_2$ (which equals 6.1 mL of O$_2$ or 30.5 mL of air). The amount of oxygen in 10 mL ethanol is 0.021 mmol (0.5 mL), which is 12 times less than necessary, thus aeration of the system is necessary.

5. Outlook. The synthesis of palladium-porphyrin directly from self-condensation of 1-acyldipyrromethane or condensation of 1,9-diacyldipyrromethane with dipyrromethane involves a single reaction where as the previous synthesis involved four reaction steps (reduction, acid-catalyzed condensation, oxidation, and palladium insertion). The previous synthesis involved a 2e$^-$+2H$^+$ reduction of each 1-acyldipyrromethane (4e$^-$+4H$^+$ overall) and 6e$^-$+6H$^+$ oxidation whereas the new synthesis involves only a 2e$^-$+2H$^+$ oxidation overall. The new synthesis avoids the use of acid (for condensation) and DDQ (for oxidation of the intermediate porphyrinogen). The new porphyrin formation involves all base reactions and thereby avoids the formation of scrambled porphyrinic products. The new palladium-porphyrin formation conditions also work reasonably for the synthesis of copper-porphyrins. In summary, although the new synthesis of metalloporphyrin works only for palladium and copper, the simplicity of the reaction conditions makes this strategy useful in porphyrin chemistry. This work extends the already diverse carbon-carbon bond-forming reactions catalyzed by palladium reagents.[25]

Because the new palladium-porphyrin formation reaction uses basic condition, this methodology can be anticipated to be useful in the condensation of acid-labile substrates (e.g., acetals, thioacetal, etc.). The limitations of these new porphyrin-forming conditions using palladium reagent are that palladium reagents are expensive, and if the free base porphyrin is desired, demetalation of palladium porphyrins requires harsh conditions that are undesirable for porphyrins that bear sensitive groups.

Experimental Section

General. $^1$H NMR (400 MHz), and $^{13}$C NMR (100 MHz) were collected routinely in CDCl$_3$ unless noted otherwise. Melting points are uncorrected. Absorption spectra were collected in toluene unless noted otherwise. Silica gel (40 μm average particle size) or alumina (80-200 mesh) was used for column chromatography. THF was distilled from sodium under argon with benzophenone/ketyl as indicator. Diethyl ether was anhydrous. Toluene, ethanol and CH$_2$Cl$_2$ (reagent grade) were used as received. All other chemicals were reagent grade and were used as received. The progress of the porphyrin-forming reactions was monitored spectroscopically in CH$_2$Cl$_2$/ethanol (3:1) solution. To determine the spectroscopic yield of palladium-porphyrin, the reaction mixture, was concentrated to dryness, dried in vacuo. Then the residue was dissolved in a known amount of THF and aliquot from this solution was diluted in CH$_2$Cl$_2$/ethanol (3:1) solution. The extent of scrambling in the crude reaction mixture was determined by laser desorption ionization mass spectrometry (LD-MS) without a matrix.[26]

Noncommercial Compounds: Dipyrromethanes 1a-c were prepared as described in the literature and analyzed for purity by gas chromatography.[14] 1-Acyldipyrromethane-boron complexes 2a,g-BR$_2$;[7] 1-acyldipyrromethanes 2a,[7] 2g,[7] 2h;[19] 1,9-diacyldipyrromethane 3a;[16] and the Mukaiyama reagents 6a-c,[16] and 6d[7] were prepared as described in the literature.

General Protocol for the Screening of Metal Reagents for Metalloporphyrin Formation. (i) From 1-Acyldipyrromethanes. A solution of 2a (43.0 mg, 0.125 mmol) in EtOH (3 mL) was treated with KOH (70.0 mg, 1.25 mmol) and metal reagent (0.063 mmol). The mixture was stirred at reflux for 1 h. The reaction was examined by UV-vis spectroscopy and TLC (silica, CH$_2$Cl$_2$) for porphyrin formation.

(ii) From 1,9-Diacyldipyrromethane+Dipyrromethane. A solution of 3a (57.0 mg, 0.125 mmol) and 1a (28.0 mg, 0.125 mmol) in EtOH (3 mL) was treated with KOH (140 mg, 2.50 mmol) and metal reagent (0.125 mmol). The mixture was stirred at reflux for 1 h. The reaction was examined by UV-vis spectroscopy and TLC (silica, CH$_2$Cl$_2$) for porphyrin formation.

General Procedure for the Self-Condensation of a 1-Acyldipyrromethane: 5,15-Bis(4-methylphenyl)-10,20-diphenylporphinatocopper(II) (Cu-5a). A mixture of 2a (85 mg, 0.25 mmol), KOH (140 mg, 2.50 mmol) and Cu(OAc)$_2$.H$_2$O (50 mg, 0.25 mmol) in ethylene glycol (3 mL) was stirred at reflux. After 8 h, the mixture was cooled to room temperature and diluted with CHCl$_3$. The mixture was then passed through a pad of silica (CHCl$_3$). The reddish fractions were collected and concentrated to afford a red-purple solid (11 mg, 13%): LD-MS obsd 703.6; FABMS obsd 703.1930, calcd 703.1923 (C$_{46}$H$_{32}$CuN$_4$). $\lambda_{abs}$ 415, 538 nm.

General Procedure for the Self-Condensation of a 1-Acyldipyrromethane: 5,15-Bis(4-methylphenyl)-10,20-diphenylporphinatopalladium(II) (Pd-5a). A sample of 2a (0.340 g, 1.00 mmol) in ethanol (10.0 mL) containing KOH (0.280 g, 5.00 mmol) and Pd(CH$_3$CN)$_2$Cl$_2$ (0.155 g, 0.600 mmol) were placed in a 25 mL round-bottom flask fitted with condenser exposed to air. The heterogeneous reaction mixture was refluxed for 1 h. The solvent was evaporated. The reaction mixture was dissolved in CH$_2$Cl$_2$ and passed through a pad of alumina (CH$_2$Cl$_2$). The resulting porphyrin-containing solution was concentrated to give an orange-purple solid. The solid was triturated with methanol and dried in vacuo, affording a crystalline orange-purple solid (0.199 g, 53%): $^1$H NMR δ 2.69 (s, 6H), 7.53 (d, J=8.0 Hz, 4H), 7.70-7.81 (m, 6H), 8.04 (d, J=8.0 Hz, 4H), 8.14-8.19 (m, 4H), 8.77-8.85 (m, 8H); $^{13}$C NMR δ 21.7, 121.8, 122.0, 126.9, 127.7, 127.9, 131.0, 131.2, 134.2, 134.3, 137.6, 139.0, 141.7, 141.9, 142.0; LD-MS obsd 746.3; FABMS obsd 746.1685, calcd 746.1661 (C$_{46}$H$_{32}$N$_4$Pd). $\lambda_{abs}$ 418, 524 nm.

General Procedure for the Condensation of a 1,9-Diacyldipyrromethane with a Dipyrromethane: 5,15-Bis(4-methylphenyl)-10,20-diphenylporphinatopalladium(II) (Pd-5a). A sample of 1a (0.111 g, 0.500 mmol) and 3a (0.229 g, 0.500 mmol) in ethanol (10.0 mL), was treated with KOH (0.280 g, 5.00 mmol) and Pd(CH$_3$CN)$_2$Cl$_2$ (0.155 g, 0.600 mmol). The mixture was refluxed for 1 h. The solvent was evaporated. The reaction mixture was dissolved in CH$_2$Cl$_2$ and passed through a pad of alumina (CH$_2$Cl$_2$). The porphyrin-containing eluant was concentrated to give an orange-purple solid. The solid was triturated with methanol and dried in vacuo, affording a crystalline orange-purple solid (0.093 g, 25%) with satisfactory characterization data ($^1$H NMR, $^{13}$C NMR, LD-MS and FABMS spectra) as described above.

Anaerobic Reactions. Each reaction was carried out under an atmosphere of argon using a Schlenk line. The ethanol was degassed prior to use by several cycles of freeze-pump-thaw using a liquid nitrogen trap and an argon atmosphere. Standard reactions were performed in a 15 mL Schlenk tube in which the solid reagents were also degassed. The ethanol was transferred to the reaction vessel with cannula and the resulting solution was stirred at 70° C. for 1 h. The progress of the porphyrin-forming reactions was monitored spectroscopically in $CH_2Cl_2$/ethanol (3:1) solution. For this, aliquots (25 μL) were periodically removed from the reaction vessel via syringe and injected into 300 μL of 10 mM oxidizing solution of DDQ in toluene. Then, a 25 μL sample from this mixture was diluted in 3000 μL of $CH_2Cl_2$/EtOH (3:1) and the visible absorption spectrum was recorded. The yield of porphyrin was determined by the intensity of the Soret band ($\epsilon_{420\ nm}$=500,000 $M^{-1}\ cm^{-1}$) measured from the apex to the inflection point at the base of the red edge of the band. A set of determinations also was done with omission of DDQ, in which case the 25 μL reaction samples were diluted in 300 μL of $CH_2Cl_2$ and the resulting solution was further diluted in 3000 μL of $CH_2Cl_2$/EtOH (3:1) to record the UV-vis spectrum.

Experiment 1 with tetrakis(triphenylphosphine)palladium (0). A Schlenk flask was charged with 2a (0.17 g, 0.50 mmol), $Pd(PPh_3)_4$ (0.35 g, 0.30 mmol) and KOH (0.14 g, 2.5 mmol). The mixture was subjected to several cycles of freeze-pump degassing with argon. Degassed ethanol was then added via cannula and the reaction mixture was heated to 70° C. for 1 h. There was no porphyrin formation according to UV-vis spectroscopy.

Experiment 2 with dichlorobis(acetonitrile)palladium(II). In a Schlenk flask were added 2a (0.17 g, 0.50 mmol), $Pd(CH_3CN)_2Cl_2$ (77 mg, 0.30 mmol) and KOH (0.14 g, 2.5 mmol). The mixture was subjected to several cycles of freeze-pump degassing with argon. Degassed ethanol was then added via cannula and the reaction mixture was heated to 70° C. After 1 h, the spectroscopic yield was 19% without adding DDQ and 16% for the aliquots exposed to oxidation with DDQ. Then the solvent was evaporated and the reaction mixture was dissolved in $CH_2Cl_2$ and passed through a pad of alumina ($CH_2Cl_2$). The resulting porphyrin-containing solution was concentrated to give an orange-purple solid. The solid was triturated with methanol and dried in vacuo, affording a crystalline orange-purple solid (60 mg, 32%): LD-MS obsd 746.0; FABMS obsd 746.1713, calcd 746.1661 ($C_{46}H_{32}N_4Pd$). $\mu_{abs}$ 416, 523 nm.

Experiment 3 with sodium hexachloropalladate (IV). A Schlenk flask containing 2a (0.17 g, 0.50 mmol), $Na_2PdCl_6$ (0.11 g, 0.30 mmol) and KOH (0.14 g, 2.5 mmol) was subjected to several cycles of freeze-pump degassing with argon. Degassed ethanol was then added via cannula and the reaction mixture was heated to 70° C. After 1 h, the solvent was evaporated. The reaction mixture was dissolved in $CH_2Cl_2$ and chromatographed (alumina, $CH_2Cl_2$). The resulting porphyrin-containing solution was concentrated to give an orange-purple solid. The solid was triturated with methanol and dried in vacuo, affording a crystalline orange-purple solid (0.013 g, 7%): LD-MS obsd 746.1; FABMS obsd 746.1706, calcd 746.1661 ($C_{46}H_{32}N_4Pd$). $\lambda_{abs}$ 416, 523 nm.

Survey of Various Solvents and Bases. A sample of 2a (34.4 mg, 100 μmol) in a given solvent (1.0 mL) containing a base (0.5 mmol) and $Pd(OAc)_2$ (13.5 mg, 60.0 μmol) was placed in a 25 mL round-bottom flask fitted with the air condenser open to the air. The resulting heterogeneous reaction mixture was refluxed for 1 h. Aliquots were periodically removed from the reaction vessel via syringe to determine the spectroscopic yield.

10-(9-Borabicyclo[3.3.1]non-9-yl)-1-(4-methoxybenzoyl)-5-phenyldipyrromethane (2b-BBN). Following a standard acylation-complexation procedure,[7] a solution of EtMgBr (20.0 mL, 20.0 mmol, 1.0 M in THF) was added slowly to a solution of 1a (2.22 g, 10.0 mmol) in THF (10 mL) under argon. The mixture was stirred at room temperature for 10 min and then cooled to −78° C. A solution of 6b (2.45 g, 10.0 mmol) in THF (10 mL) was added. The solution was stirred at −78° C. for 10 min and then warmed to room temperature. After standard workup, the crude product (a red-orange oil) thus obtained was dissolved in $CH_2Cl_2$ (20 mL) and treated with TEA (3.35 mL, 24.0 mmol) followed by 9-BBN-OTf (40.0 mL, 20.0 mmol, 0.5 M in hexanes) with stirring at room temperature. After 1 h, the mixture was passed through a pad of silica ($CH_2Cl_2$), affording a yellow solid (2.96 g, 62%): mp 178-180° C.; $^1H$ NMR δ 0.62-0.73 (m, 2H), 1.62-1.84 (m, 6H), 1.86-2.31 (m, 6H), 3.92 (s, 3H), 5.30 (s, 1H), 5.83-5.88 (m, 1H), 6.01 (s, 1H), 6.13-6.18 (m, 1H), 6.39 (d, J=4.0 Hz, 1H), 6.69-6.75 (m, 1H), 7.05 (d, J=8.0 Hz, 2H), 7.13-7.37 (m, 5H), 7.78-7.94 (br, 1H), 8.21 (d, J=8.0 Hz, 2H); $^{13}C$ NMR δ 23.9, 25.1, 26.0, 26.4, 30.6, 30.9, 34.6, 34.7, 44.8, 55.8, 108.1, 108.6, 114.6, 117.4, 117.7, 120.5, 123.5, 127.0, 128.5, 128.7, 132.0, 132.5, 134.5, 142.3, 151.2, 164.4, 173.9. Anal. Calcd for $C_{31}H_{33}BN_2O_2$: C, 78.15; H, 6.98; N, 5.88. Found: C, 78.07; H, 7.00; N, 5.73. $\lambda_{abs}$ 386 nm.

10-(Dibutylboryl)-1-(pentafluorobenzoyl)-5-phenyldipyrromethane ($2c-BBu_2$). Following a standard acylation-complexation procedure,[7] a solution of EtMgBr (5.0 mL, 5.0 mmol, 1.0 M in THF) was added slowly to a solution of 1a (0.222 g, 1.00 mmol) in THF (1 mL) under argon. The mixture was stirred at room temperature for 10 min and then cooled to −78° C. A solution of 6c (0.304 g, 1.00 mmol) in THF (1 mL) was added. The solution was stirred at −78° C. for 10 min and then warmed to room temperature. After standard workup, the crude product (a red-orange oil) thus obtained was dissolved in $CH_2Cl_2$ (2 mL) and treated with TEA (0.35 mL, 2.4 mmol) followed by $BBu_2$-OTf (2 mL, 2 mmol, 0.5 M in hexanes) with stirring at room temperature. After 1 h, the mixture was passed through a pad of silica ($CH_2Cl_2$), affording a brownish-yellow paste (0.295 g, 55%): $^1H$ NMR δ 0.38-0.54 (m, 2H), 0.59-0.69 (m, 6H), 0.70-1.26 (m, 6H), 1.54 (s, 3H), 5.58 (s, 1H), 5.85-5.91 (m, 1H), 6.14-6.16 (m, 1H), 6.49-6.54 (m, 1H), 6.68-6.73 (m, 1H), 7.03-7.09 (m, 1H), 7.21-7.39 (m, 5H), 7.75-7.86 (br, 1H); $^{13}C$ HMR δ 14.2, 14.3, 26.0, 26.1, 26.8, 27.2, 44.4, 108.2, 108.9, 117.4, 117.8, 119.9, 121.7, 127.6, 128.7, 129.1, 139.6, 140.6; FABMS obsd 541.2444, calcd 541.2450 ($C_{30}H_{30}BF_5N_2O$). $\lambda_{abs}$ 315 nm.

10-(9-Borabicyclo[3.3.1]non-9-yl)-1-hexanoyl-5-phenyldipyrromethane (2d-BBN). Following a standard acylation-complexation procedure,[7] a solution of EtMgBr (20.0 mL, 20.0 mmol, 1.0 M in THF) was added slowly to a solution of 1a (2.22 g, 10.0 mmol) in THF (10 mL) under argon. The mixture was stirred at room temperature for 10 min and then cooled to −78° C. A solution of 6d (2.09 g, 10.0 mmol) in THF (10 mL) was added. The solution was stirred at −78° C. for 10 min and then warmed to room temperature. After standard workup, the crude product (a red-orange oil) thus obtained was dissolved in $CH_2Cl_2$ (20 mL) and treated with TEA (3.35 mL, 24.0 mmol) followed by 9-BBN-OTf (40.0 mL, 20.0 mmol, 0.5 M in hexanes) with stirring at room temperature. After 1 h, the mixture was passed through a pad of silica eluting with $CH_2Cl_2$, followed by concentration afforded a yellow paste (1.95 g, 42%): $^1H$ NMR δ 0.55-0.58

(m, 2H), 0.86-1.00 (m, 3H), 1.28-1.43 (m, 4H), 1.60-2.20 (m, 14H), 2.80-2.87 (m, 2H), 5.80-5.84 (m, 1H), 5.94 (s, 1H), 6.09-6.15 (m, 1H), 6.28-6.33 (m, 1H), 6.66-6.71 (m, 1H), 7.05-7.06 (m, 1H), 7.12-7.18 (m, 2H), 7.19-7.39 (m, 3H), 7.78-7.83 (br 1H); $^{13}$C NMR δ 14.1, 22.5, 23.9, 25.0, 25.5, 25.6, 25.9, 26.3, 30.6, 30.9, 31.5, 31.9, 34.2, 34.3, 44.8, 108.1, 108.6, 117.1, 117.5, 119.9, 127.1, 128.5, 128.7, 132.4, 136.9, 142.2, 152.2, 185.2; FABMS obsd 440.3012, calcd 440.2999 ($C_{29}H_{37}BN_2O$). $\lambda_{abs}$ 338 nm.

1-(Benzoyl-carbonyl-$^{13}$C)-10-(9-borabicyclo[3.3.1]non-9-yl)-5-phenyldipyrromethane (2f-BBN). Following a standard procedure,[7] a solution of EtMgBr (10 mL, 10 mmol, 1.0 M in THF) was carefully added to a stirred solution of 5-phenyldipyrromethane (1a) (1.22 g, 4.90 mmol) in THF (5 mL) under argon. The mixture was stirred at room temperature for 10 min and then cooled to −78° C. A solution of 6f (1.06 g, 4.90 mmol) in THF (5 mL) was then added over 1 min. The solution was maintained at −78° C. for 10 min, then the mixture (orange oil) was allowed to warm to room temperature. After standard workup, the crude product obtained was dissolved in $CH_2Cl_2$ (10 mL) and treated with TEA (1.6 mL, 12 mmol) and 9-BBN-OTf (20 mL, 10 mmol, 0.5 M hexanes) while stirring at room temperature. After 1 h, the reaction mixture was passed through a silica pad ($CH_2Cl_2$), affording an yellow solid (1.54 g, 70%): mp 175-180° C.; $^1$H NMR δ 0.64-0.76 (m, 2H), 1.64-1.88 (m, 6H), 1.92-2.30 (m, 6H), 5.84-5.86 (m, 1H), 6.02 (s, 1H), 6.13-6.18 (m, 1H), 6.42-6.46 (m, 1H), 6.70-6.76 (m, 1H), 7.15-7.20 (m, 2H), 7.23-7.37 (m, 4H), 7.54-7.60 (m, 2H), 7.62-7.68 (m, 1H), 7.82-7.90 (br, 1H), 8.18-8.24 (m, 2H); $^{13}$C NMR δ 23.9, 25.2, 30.7, 30.8, 34.5, 34.6, 44.8, 108.2, 108.7, 117.6, 118.6, 118.7, 121.2, 121.3, 127.2, 128.6, 128.8, 129.2, 129.3, 129.76, 129.79, 133.9, 142.1, 174.4; FABMS obsd 447.2551, calcd 447.2563 ($C_{29}{}^{13}CH_{31}BN_2O$). $\lambda_{abs}$ 332 nm. 1-(4-Methoxybenzoyl)-5-phenyldipyrromethane (2b). Following a standard procedure,[7] a sample of 2b-BBN (2.38 g, 5.00 mmol) in THF (8.0 mL) and 1-pentanol (2.0 mL) was refluxed for 1.5 h. The mixture was concentrated. The residue was dissolved in a small volume of $CH_2Cl_2$ (2.0 mL) and treated with hexanes, affording a brown paste. The solvent was decanted and the residue was dried in vacuo, washed thoroughly with hexanes, and dried to afford a pale brown amorphous powder (1.45 g, 81%): mp 55-57° C.; $^1$H NMR δ 3.87 (s, 3H), 5.54 (s, 1H), 5.96-6.01 (m, 1H), 6.05-6.12 (m, 1H), 6.14-6.18 (m, 1H), 6.67-6.72 (m, 1H), 6.78-6.82 (m, 1H), 6.94 (d, J=8.0 Hz, 2H), 7.18-7.35 (m, 5H), 7.84 (d, J=8.0 Hz, 2H), 8.10-8.26 (br, 1H), −9.59-9.73 (br, 1H); $^{13}$C NMR δ 44.2, 55.6, 107.8, 108.4, 110.6, 113.7, 117.9, 120.4, 127.3, 128.4, 128.8, 130.8, 131.1, 131.3, 141.0, 141.5, 162.8, 183.7; FABMS obsd 356.1524, calcd 356.1549 ($C_{23}H_{20}N_2O_2$). Anal. Calcd for $C_{23}H_{20}N_2O_2$: C, 77.51; H, 5.66; N, 7.86. Found: C, 73.37; H, 5.89; N, 6.99.

1-Pentafluorobenzoyl-5-phenyldipyrromethane (2c). Following a standard procedure,[7] a sample of 2c-BBu$_2$ (0.230 g, 0.425 mmol) in 1-pentanol (1 mL) was heated at 70-75° C. After 4 h the boron complex was still present in reaction mixture, as proven by TLC. The reaction mixture was stirred overnight at room temperature. The mixture was concentrated, and the residue was dissolved in a small volume of $CH_2Cl_2$ (2.0 mL) and treated with hexanes, affording a brown paste. The product was chromatographed (silica, $CH_2Cl_2$), affording a pale golden-brown amorphous powder (295 mg, 55%): mp 48-56° C.; $^1$H NMR δ 5.55 (s, 1H), 5.96-6.00 (m, 1H), 6.09-6.19 (m, 2H), 6.63-6.67 (m, 1H), 6.68-6.72 (m, 1H), 7.16-7.20 (m, 2H), 7.23-7.34 (m, 3H), 8.10-8.19 (br, 1H), 9.96-10.2 (br, 1H); $^{13}$C NMR δ 44.4, 108.3, 108.9, 112.1, 118.3, 123.1, 127.8, 128.6, 129.2, 130.4, 131.1, 140.3, 145.3, 171.9; FABMS obsd 416.0965, calcd 416.0948 ($C_{22}H_{13}F_5N_2O$). Anal. Calcd for $C_{22}H_{13}F_5N_2O$: C, 63.47; H, 3.15; N, 6.73. Found: C, 63.78; H, 3.46; N, 6.53.

1-Hexanoyl-5-phenyldipyrromethane (2d). Following a standard procedure,[7] a sample of 2d-BBN (1.95 g, 4.20 mmol) in THF (6.3 mL) and 1-pentanol (2.2 mL) was refluxed for 2 h. The mixture was concentrated. The residue was dissolved in a small volume of $CH_2Cl_2$ (2.0 mL) and treated with hexanes, affording a brown paste. The solvent was decanted and the residue was dried in vacuo, washed thoroughly with hexanes, and dried again to afford a brown paste (0.96 g, 30%): $^1$H NMR δ 0.83-0.91 (m, 3H), 1.24-1.40 (m, 2H), 1.58-1.72 (m, 2H), 2.56-2.72 (m, 2H), 5.49 (s, 1H), 5.94-5.96 (m, 1H) 5.98-6.04 (m, 1H), 6.12-6.18 (m, 1H), 6.68-6.73 (m, 1H), 6.80-6.86 (m, 1H), 7.13-7.34 (m, 5H), 8.15-8.20 (br, 1H), 9.40-9.45 (br, 1H); $^{13}$C NMR δ 14.1, 22.7, 25.4, 31.9, 37.9, 44.3, 107.9, 108.7, 110.2, 117.2, 117.9, 127.5, 128.5, 129.0, 131.2, 131.7, 140.6, 141.0, 191.2; FABMS obsd 320.1906, calcd 320.1889 ($C_{21}H_{24}N_2O$). The characterization data are consistent with reported values for the product from the synthesis via a different route.[28]

1-(2,4,6-Trimethylbenzoyl)-5-phenyldipyrromethane (2e). Following a standard procedure,[15] a solution of 1a (2.22 g, 10.0 mmol) in THF (10 mL) at room temperature under Ar was treated with EtMgBr (25 mL, 25 mmol, 1.0 M solution in THF) for 10 min. The solution was cooled to −78° C. Then a solution of 6e (2.57 g, 10.0 mmol) in THF (10.0 mL) was added. The reaction mixture was stirred at −78° C. for 10 min and at room temperature for 20 min. Standard workup and chromatography [silica, $CH_2Cl_2$/ethyl acetate (9:1)] afforded a colorless solid (2.48 g, 67%): mp 200-202° C.; $^1$H NMR δ 2.15 (s, 6H), 2.30 (s, 3H), 5.51 (s, 1H), 5.94-6.01 (m, 1H), 6.15-6.20 (m, 1H), 6.34-6.44 (m, 1H), 6.68-6.72 (m, 1H), 6.85 (s, 1H), 7.21-7.39 (m, 7H), 7.96-8.12 (br, 1H), 9.21-9.35 (br, 1H); $^{13}$C NMR δ 19.3, 21.1, 44.2, 107.7, 108.3, 110.7, 117.8, 120.9, 127.3, 128.1, 128.3, 128.8, 130.6, 132.1, 134.47, 134.50, 136.5, 138.2, 140.6, 142.0, 188.9. Anal. Calcd for $C_{25}H_{24}N_2O$: C, 81.49; H, 6.57; N, 7.60. Found: C, 81.44; H, 6.57; N, 7.67.

1-(Benzoyl-carbonyl-$^{13}$C)-5-phenyldipyrromethane (2f). According to a known procedure,[7] a solution of 2f-BBN (1.54 g, 3.50 mmol) in THF (5.5 mL) and 1-pentanol (2.6 mL) was refluxed for 3.5 h. The reaction was cooled to room temperature and concentrated. The crude product was treated with hexanes (30 mL), heated until completely dissolved and was cooled to room temperature. The resulting precipitate was separated, dissolved in $CH_2Cl_2$ and dried to give a pale-brown amorphous powder (1.067 g, 67%): mp 56-62° C.; $^1$H NMR δ 55.56 (s, 1H), 5.97-6.00 (m, 1H), 6.08-6.16 (m, 2H), 6.62-6.65 (m, 1H), 6.78-6.82 (m, 1H), 7.16-7.30 (m, 5H), 7.40-7.48 (m, 2H), 7.50-7.58 (m, 1H), 7.74-7.80 (m, 2H), 8.35-8.42 (br, 1H), 10.10-10.15 (br, 1H); $^{13}$C NMR δ 44.4, 108.0, 108.8, 110.7, 110.8, 118.0, 120.7, 120.8, 127.6, 128.4, 128.5, 128.6, 129.0, 129.1, 131.9, 140.8, 169.4, 184.7; FABMS obsd 327.1467, calcd 327.1453 ($C_{21}{}^{13}C_1H_{18}N_2O$).

1-[(α-Hydroxy)benzyl-methyl-$^{13}$C]-5-phenyldipyrromethane (2f-OH). Following a known procedure,[15] a sample of NaBH$_4$ (116 mg, 3.06 mmol) was added in small portions to a stirred solution of 2f (40 mg, 0.12 mmol) in THF/methanol (3:1, 2.5 mL). After 20 min the usual workup afforded the crude carbinol as an orange oil. $^{13}$C NMR of the crude 2f-OH showed the chemical shift at 70.45 ppm for the $^{13}$C-labeled carbon.

1-(4-methylbenzoyl)-5-phenyldipyrrin (4a). Following a standard procedure,[17] a solution of 2a (1.7 g, 5.0 mmol) in THF (16 mL) was treated dropwise with a solution of DDQ (1.13 g, 5.00 mmol) in THF (16 mL). After stirring for 1 h at room temperature, the solvent was evaporated. The reaction mixture was dissolved in $CH_2Cl_2$ and purified by column chromatography [silica, $CH_2Cl_2$/ethyl acetate (25:1)], affording a pale brown amorphous powder (1.15 g, 68%): mp 120-122° C.; $^1$H NMR δ 2.44 (s, 3H), 6.38 (d, J=4 Hz, 1H), 6.57 (d, J=4 Hz, 1H), 6.79-6.85 (m, 2H), 7.30 (d, J=8 Hz, 2H), 7.43-7.54 (m, 5H), 7.87 (d, J=8 Hz, 2H), 8.09 (s, 1H), 12.90-13.40 (br, 1H); $^{13}$C NMR δ 21.8, 119.0, 122.2, 125.4, 128.0, 129.2, 129.3, 129.5, 130.9, 135.0, 135.6, 136.7, 138.2, 139.3, 140.4, 143.0, 150.6, 159.6, 185.4. Anal. Calcd for $C_{23}H_{18}N_2O$: C, 81.63; H, 5.36; N, 8.28. Found: C, 81.70; H, 5.33; N, 8.24. $\lambda_{abs}$ ($CH_2CL_2$) 301, 433 nm.

5,15-Bis(4-methoxyphenyl)-10,20-diphenylporphinatopalladium(II) (Pd-5b). Self-condensation of 2b (0.356 g, 1.00 mmol) in ethanol (10.0 mL) in presence of KOH (0.280 g, 5.00 mmol) and $Pd(CH_3CN)_2Cl_2$ (0.155 g, 0.600 mmol) following the procedure described for Pd-5a gave a purple solid. The solid was triturated with methanol and dried in vacuo affording a crystalline purple solid (0.148 g, 38%): $^1$H NMR δ 4.08 (s, 6H), 7.23-7.31 (m, 4H), 7.69-7.81 (m, 6H), 8.04-8.11 (m, 4H), 8.14-8.20 (m, 4H), 8.78-8.87 (m, 8H); $^{13}$C NMR δ 55.8, 112.4, 121.7, 121.8, 126.9, 127.9, 131.1, 131.2, 134.3, 135.3, 141.7, 142.0, 142.1, 159.6; LD-MS obsd 778.1; FABMS obsd 778.1611, calcd 778.1560 ($C_{46}H_{32}N_4O_2Pd$). $\lambda_{abs}$ 419, 525 nm.

5,15-Bis(4-ethoxy-2,3,5,6-tetrafluorophenyl)-10,20-diphenylporphinatopalladium(II) (Pd-5c). Self-condensation of 2c (0.380 g, 1.00 mmol) in ethanol (10.0 mL) containing KOH (0.280 g, 5.00 mmol) and $Pd(CH_3CN)_2Cl_2$ (0.155 g, 0.600 mmol) following the procedure described for Pd-5a gave a purple solid. The solid was triturated with methanol and dried in vacuo affording a crystalline purple solid (0.138 g, 29%): $^1$H NMR δ 1.63-1.67 (m, 6H), 4.61-4.68 (m, 4H), 7.72-7.84 (m, 6H), 8.16-8.22 (m, 4H), 8.78-8.82 (m, 4H), 8.88-8.91 (m, 4H); $^{13}$C NMR δ 15.9, 29.9, 122.8, 127.1, 128.2, 129.8, 132.7, 134.4, 141.3, 141.4, 142.4; LD-MS obsd 952.1; FABMS obsd 950.1174, calcd 950.1119 ($C_{48}H_{28}F_8N_4O_2Pd$). $\lambda_{abs}$ 414, 522 nm.

5,15-Dipentyl-10,20-diphenylporphinatopalladium(II) (Pd-5d). Self-condensation of 2d (0.320 g, 1.00 mmol) in ethanol (10.0 mL) containing KOH (0.280 g, 5.00 mmol) and $Pd(CH_3CN)_2Cl_2$ (0.155 g, 0.600 mmol) following the procedure described for Pd-5a gave an orange-purple solid. The solid was triturated with methanol and dried in vacuo affording a crystalline purple solid (0.172 g, 49%): $^1$H NMR δ 0.92-1.00 (m, 6H), 1.49-159 (m, 4H), 1.72-1.82 (m, 4H), 2.44-2.23 (m, 4H), 4.85-4.93 (m, 4H), 7.72-7.80 (m, 6H), 8.14-8.18 (m,4H), 8.82-8.85 (m, 4H), 9.39-9.42 (m, 4H); $^{13}$C NMR δ 14.4, 22.9, 32.9, 35.5, 38.2, 120.8, 121.4, 126.8, 127.8, 127.9, 131.5, 134.2, 140.8, 141.7, 142.3; LD-MS obsd 706.5; FABMS obsd 706.2338, calcd 706.2288 ($C_{42}H_{40}N_4Pd$). $\lambda_{abs}$ 417, 525 nm.

meso-(5,15-$^{13}$C)Tetraphenylporphinatopalladium(II) (Pd-5f). A sample of 2f (0.326 g, 0.100 mmol) was reacted in $EtOH-d_6$ (1 mL) containing KOH (28 mg, 0.50 mmol) and $Pd(CH_3CN)_2Cl_2$ (15 mg, 0.060 mmol) in an NMR tube under the standard conditions, affording the title compound: $^1$H NMR δ 7.70-7.80 (m, 12H), 8.16-8.20 (m, 8H), 8.81 (s, 8H); $^{13}$C NMR δ 121.9, 126.9, 127.9, 131.1, 131.2, 134.3, 141.4, 141.70, 141.74, 141.8, 141.9, 142.1, 142.3; LD-MS obsd 720.3; FABMS obsd 720.1442, calcd 720.1416 ($C_{42}{}^{13}C_2H_{28}N_4Pd$). $\lambda_{abs}$ 415, 52 nm.

meso-Tetrakis(4-methoxyphenyl)porphinatopalladium (II) (Pd-5g). Self-condensation of 2g (0.386 g, 1.00 mmol) in ethanol (10.0 mL) containing KOH (0.280 g, 5.00 mmol) and $Pd(CH_3CN)_2Cl_2$ (0.155 g, 0.600 mmol) following the procedure described for Pd-5a gave a purple crystalline solid. The solid was triturated with methanol and dried in vacuo affording a crystalline purple solid (0.185 g, 44%): $^1$H NMR δ 4.09 (s, 12H), 7.24-7.31 (m, 8H), 8.07 (d, J=8.4 Hz, 8H), 8.83 (s, 8H); $^{13}$C NMR δ 55.8, 112.4, 121.6, 131.1, 134.4, 135.3, 142.6, 159.6; LD-MS obsd 838.2; FABMS obsd 838.1815, calcd 838.1771 ($C_{48}H_{36}N_4O_4Pd$). $\lambda_{abs}$ 421, 526 nm. A different route to synthesize this compound has been reported earlier.[29]

5,15-Diphenylporphinatopalladium(II) (Pd-5i). Self-condensation of 2i (0.250 g, 1.00 mmol) in ethanol (10.0 mL) containing KOH (0.280 g, 5.00 mmol) and $Pd(CH_3CN)_2Cl_2$ (0.155 g, 0.600 mmol) following the procedure described for Pd-5a gave a orange-purple solid. The solid was triturated with methanol and dried in vacuo affording a crystalline orange-purple solid (0.162 g, 57%): $^1$H NMR δ 7.74-7.77 (m, 6H), 8.18-8.27 (m, 4H), 9.01 (d, J=5.0 Hz, 4H), 9.30 (d, J=5.0 Hz, 4H), 10.29 (s, 2H); $C^{13}$C NMR δ 107.3, 109.4, 127.0, 128.0, 131.2, 131.7, 134.5, 141.3, 141.5, 141.8; LD-MS obsd 565.3; FABMS obsd 566.0746, calcd 566.0722 ($C_{32}H_{20}N_4Pd$). $\lambda_{abs}$ 405, 513 nm.

S-2-Pyridyl 2,4,6-trimethylbenzothioate (6e). Following a standard procedure,[16] a solution of 2-mercaptopyridine (3.33 g, 30.0 mmol) in THF (30 mL) was treated with p-mesitoyl chloride (5.48 g, 30.0 mmol) at room temperature with stirring for 30 min. The standard workup followed by precipitation afforded a pale yellow solid (6.32 g, 82%): mp 48-50° C. (lit.[4] 54-55° C.): $^1$H NMR δ 2.30 (s, 3H), 2.40 (s, 6H), 6.86-6.91 (m, 2H), 7.29-7.35 (m, 1H), 7.76-7.83 (m, 2H), 8.64-8.69 (m, 1H); $^{13}$C NMR δ 19.2, 21.3, 123.7, 128.6, 130.0, 133.9, 137.0, 137.3, 139.9, 150.6, 152.1, 195.3. Anal. Calcd for $C_{15}H_{15}NOS$: C, 70.01; H, 5.87; N, 5.44. Found: C, 70.10; H, 5.95; N, 5.38. The title compound has been prepared via a different route; the reported characterization data ($^1$H NMR spectrum) are consistent with those observed here.[30]

$^{13}$C—S-2-Pyridyl benzothioate (6f). Following a standard procedure,[18, 19] a solution of benzoic acid (carboxyl-$^{13}$C) (1.0 g, 8.0 mmol) in THF (40 ml) under argon was treated with 2,2'-dipyridyl disulfide (2.6 g, 12 mmol) and triphenylphosphine (3.2 g, 12 mmol) at room temperature. The starting material was still present after 24 h, 36 h and 48 h. After 48 h, the reaction was stopped and worked up to give a yellow solid (0.99 g, 56%): mp 47-49° C.; $^1$H NMR δ 7.32-7.38 (m, 1H), 7.46-7.54 (m, 2H), 7.60-7.68 (m, 1H), 7.72-7.76 (m, 1H), 7.78-7.83 (m, 1H), 8.00-8.06 (m, 2H), 8.67-8.71 (m, 1H); $^{13}$C NMR δ 123.8, 127.7, 127.8, 129.02, 129.06, 131.1, 134.1, 137.4, 150.7, 189.6; FABMS obsd 217.0503, calcd 217.0517 ($C_{11}{}^{13}C_1H_9NOS$).

S-2-Pyridyl benzothioate (6g). Following a standard procedure,[16] a solution of 2-mercaptopyridine (3.33 g, 30.0 mmol) in THF (30 mL) was treated with benzoyl chloride (4.21 g, 30.0 mmol) at room temperature with stirring for 30 min. The standard workup followed by precipitation afforded a pale yellow solid (5.67 g, 88%): mp 48-50° C. $^1$H NMR spectral data are consistent with reported values:[15] $^1$H NMR δ 7.31-7.37 (m, 1H), 7.46-7.53 (m, 2H), 7.59-7.65 (m, 1H), 7.71-7.83 (m, 2H), 8.00-8.06 (m, 2H), 8.66-8.71 (m, 1H); $^{13}$C NMR δ 123.7, 127.6, 128.9, 131.0, 134.0, 136.6, 137.3, 150.6, 151.4, 189.4. Anal. Calcd for $C_{12}H_9NOS$: C, 66.95; H, 4.21; N, 6.51. Found: C, 66.63; H, 4.12; N, 6.57.

REFERENCES (1) Tamaru, S.-I.; Yu, L.; Youngblood, W. J.; Muthukumaran, K.; Taniguchi, M.; Lindsey, J. S. *J. Org. Chem.* 2004, 69, 765-777.
(2) Mehta, P.; Mehta, R. K. *J. Indian Chem. Soc.* 1984, LXI, 571-572.
(3) Adams, H.; Bailey, N. A.; Fenton, D. E.; Moss, S.; Rodriguez de Barbarin, C. O. *J. Chem. Soc. Dalton Trans.* 1986, 693-699.
(4) Tayim, H. A.; Salameh, A. S. *Polyhedron* 1986, 5, 687-689.
(5) Dawson, D. M.; Walker, D. A.; Thornton-Pett, M.; Bochmann, M. *J. Chem. Soc. Dalton Trans.* 2000, 459-466.
(6) Bacchi, A.; Bonardi, A.; Carcelli, M.; Mazza, P.; Pelagatti, P.; Pelizzi, C.; Pelizzi, G.; Solinas, C.; Zani, F. *J. Inorg. Biochem.* 1998, 69, 101-112.
(7) Muthukumaran, K.; Ptaszek, M.; Noll, B.; Scheidt, W. R.; Lindsey, J. S. *J. Org. Chem.* 2004, 69, 5354-5364.
(8) Papkovsky, D. B.; O'Riordan, T.; Soini, A. *Biochem. Soc. Trans.* 2000, 28, 74-77.
(9) Borisov, S. M.; Vasil'ev, V. V. *J. Anal. Chem.* 2004, 59, 155-159.
(10) Wiehe, A.; Stollberg, H.; Runge, S.; Paul, A.; Senge, M. O.; Roder, B. *J. Porphyrins Phthalocyanines* 2001, 5, 853-860.
(11) Kim, K.; Fancy, D. A.; Carney, D.; Kodadek, T. *J. Am. Chem. Soc.* 1999, 121, 11896-11897.
(12) Thomas, D. W.; Martell, A. E. *J. Am. Chem. Soc.* 1959, 81, 5111-5119.
(13) Buchler, J. W. In *Porphyrins and Metalloporphyrins*; Smith, K. M. Ed.; Elsevier Scientific Publishing Co.: Amsterdam 1975, pp. 157-231.
(14) Laha, J. K.; Dhanalekshmi, S.; Taniguchi, M.; Ambroise, A.; Lindsey, J. S. *Org. Process Res. Dev.* 2003, 7, 799-812.
(15) Rao, P. D.; Littler, B. J.; Geier, G. R., III; Lindsey, J. S. *J. Org. Chem.* 2000, 65, 1084-1092.
(16) Zaidi, S. H. H.; Muthukumaran, K.; Tamaru, S.-I.; Lindsey, J. S. *J. Org. Chem.* 2004, 69, in press.
(17) Yu, L.; Muthukumaran, K.; Sazanovich, I. V.; Kirmaier, C.; Hindin, E.; Diers, J. R.; Boyle, P. D.; Bocian, D. F.; Holten, D.; Lindsey, J. S. *Inorg. Chem.* 2003, 42, 6629-6647.
(18) Araki, M.; Sakata, S.; Takei, H.; Mukaiyama, T. *Bull. Chem. Soc. Jpn.* 1974, 47, 1777-1780.
(19) Rao, P. D.; Dhanalekshmi, S.; Littler, B. J.; Lindsey, J. S. *J. Org. Chem.* 2000, 65, 7323-7344.
(20) Bruckner, C.; Posakony, J. J.; Johnson, C. K.; Boyle, R. W.; James, B. R.; Dolphin, D. J. *J. Porphyrins Phthalocyanines* 1998, 2, 455-465.
(21) Battioti, P.; Brigaud, O.; Desvaux, H.; Mansuy, D.; Traylor, G. T. *Tetrahedron Lett.* 1991, 25, 2893-2896.
(22) Kadish, K. M.; Araullo-McAdams, C.; Han, B. C.; Franze, M. M. *J. Am. Chem. Soc.* 1990, 112, 8364-8368.
(23) Littler, B. J.; Miller, M. A.; Hung, C.-H.; Wagner, R. W.; O'Shea, D. F.; Boyle, P. D.; Lindsey, J. S. *J. Org. Chem.* 1999, 64, 1391-1396.
(24) Kral, V.; Sessler, J. L.; Zimmerman, R. S.; Seidel, D.; Lynch, V.; Andrioletti, B. *Angew. Chem. Int. Ed.* 2000, 39, 1055-1058.
(25) (a) Nishimura, T.; Uemura, S. *Synlett* 2004, 201-216. (b) Stoltz, B. M. *Chem. Lett.* 2004, 33, 362-367. (c) Stahl, S. S. *Angew. Chem. Int. Ed.* 2004, 43, 3400-3420.
(26) Srinivasan, N.; Haney, C. A.; Lindsey, J. S.; Zhang, W.; Chait, B. T. *J. Porphyrins Phthalocyanines* 1999, 3, 283-291.
(27) Du, H.; Fuh, R.-C. A.; Li, J.; Corkan, L. A.; Lindsey, J. S. *Photochem. Photobiol.* 1998, 68, 141-142.
(28) Geier, G. R. III; Callinan, J. B.; Rao, P. D.; Lindsey, J. S. *J. Porphyrins Phthalocyanines* 2001, 5, 810-823.
(29) Honeybourne, C. L.; Hill, C. A. S. *J. Phys. Chem. Solids* 1998, 49, 315-321.
(30) Imamoto, T.; Kodera, M.; Yokoyama, M. *Synthesis* 1982, 134-136.
(31) Hong, S.-H.; Ka, J.-W.; Won, D.-H.; Lee, C.-H. *Bull. Korean Chem. Soc.* 2003, 24, 661-663.

The foregoing is illustrative of the present invention, and is not to be construed as limiting thereof. The invention is defined by the following claims, with equivalents of the claims to be included therein.

That which is claimed is:

1. A method of making a porphyrin-metal complex, comprising:
    (a) providing a first reagent selected from the group consisting of 1-acyldipyrromethanes, 1-acyldipyrrins, and dipyrromethane-1-carbinols; and then
    (b) condensing said first reagent with itself in a reaction mixture comprising a solvent and a second reagent selected from the group consisting of palladium and copper complexes to produce a porphyrin-metal complex, wherein said metal is selected from the group consisting of palladium and copper.

2. The method of claim 1, wherein said first reagent is a 1-acyldipyrromethane.

3. The method of claim 1, wherein said first reagent is a 1-acyldipyrrin.

4. The method of claim 1, wherein said first reagent is a dipyrromethane-1-carbinol.

5. The method of claim 1, wherein said second reagent is a copper 0, copper I, copper II, or copper III complex.

6. The method of claim 1, wherein said second reagent is a palladium 0, palladium II, or palladium IV complex.

7. The method of claim 1, wherein said second reagent is a palladium II or palladium IV complex.

8. The method of claim 1, wherein said second reagent is a palladium II or palladium IV complex selected from the group consisting of $PdX_2$, $PdX_2L_2$, $PdX_2L_4$, and $PdX_4Y_2Z_2$, wherein X is an anion, L is a neutral group; Y is a cation, and Z is an anion.

9. The method of claim 1, wherein said second reagent is a palladium II or palladium IV complex selected from the group consisting of: $K_2PdCl_6$, $Na_2PdCl_6$, $(NH_4)_2PdCl_6$, $Pd(OAc)_2$, $Pd(acac)_2$, $PdCl_2$, $PdBr_2$, $Pd(CN)_2$, $PdI_2$, PdO, $PdO \cdot xH_2O$, PdS, $Pd(O_2CCF_3)_2$, $C_3H_5PdCl_2$, $(NH_4)_2PdCl_4$, $Pd(NO_3)_2 \cdot xH_2O$, $PdSO_4 \cdot H_2O$, $K_2PdBr_4$, $K_2PdCl_4$, $Na_2PdCl_4$, $K_2Pd(S_2O_3)_2 \cdot H_2O$, $(CH_3CO_2)_2Pd[P(C_6H_5)_3]_2$, $Pd(NH_3)_2(NO_2)_2$, $Pd(NH_3)_2(NO_3)_2$, $[Pd(NH_3)_4][PdCl_4]$, $Pd(NH_3)_2Cl_2$, $PdCl_2(CH_3CN)_2$, $PdCl_2[P(C_6H_5)_3]_2$, $PdCl_2(C_6H_5CN)_2$, $Pd(O_2CC_2C_2H_5)_2$, $PdCl_2[P(C_6H_{11})_3]_2$, $PdCl_2[P(C_6H_5)_3]_2$, $PdCl_2[P(CH_3C_6H_5)_3]_2$, $Pd(BF_4)_2(CH_3CN)_4$, trans-di(μ-acetato)bis[o-(di-o-tolyl-phosphino)benzyl]dipalladium, dichloro(1,2-bis(diphenylphosphino)ethane)palladium(II), dichloro[1,1'-bis(diphenylphosphino)ferrocene]palladium(II)dichloromethane adduct, palladium(II) hexafluoroacetylacetonate, dichloro(1,5-cyclooctadiene)palladium(II), ammonium bis(oxalato)palladium(II), dichloro(ethylenediamine)palladium(II), bis(pyridine)palladium(II)chloride, chloro(di-2-norbornylphosphino)(2-dimethylaminomethylferrocen-1-yl)palladium(II), chloro(di-2-norbornylphosphino)(2'-dimethylamino-1,1'-biphenyl-2-yl)

palladium(II), dichloro(1,3-bis(diphenylphosphino) propane)palladium(II), bis[tris(4-(1H, 1H,2H,2H-perfluorodecyl)phenyl)phosphine]palladium(II)dichloride, benzylbis(triphenylphosphine)palladium(II)chloride, (bicyclo[2.2.1]hepta-2,5-diene)dichloropalladium(II), ([2S,3S]-bis[diphenylphosphino]butane)(eta$^3$-allyl)palladium(II)perchlorate, acetato(2'-di-t-butylphosphino-1,1'-biphenyl-2-yl) palladium(II), allylchloro[1,3-bis(2,6-di-isopropylphenyl) imidazol-2-ylidene]palladium(II).

10. The method of claim 1, wherein said second reagent is selected from the group consisting of $Pd(OAc)_2$, $Pd(acac)_2$, $Pd(CH_3CN)_2Cl_2$, $PdBr_2$ and $PdCl_2$.

11. The method of claim 1, wherein said solvent is an alcohol solvent, ethereal solvent, tetrahydrofuran, water, or mixture thereof.

12. The method of claim 1, wherein said solvent is ethanol.

13. The method of claim 1, wherein said reaction mixture further comprises a base.

14. The method of claim 1, wherein said reaction mixture further comprises a base selected from the group consisting of KOH and NaH.

15. The method of claim 1, wherein said reaction mixture has a pH of at least 7.

16. The method of claim 1, wherein said reaction mixture comprises not more than 0.5 percent by weight added acid.

17. The method of claim 1, wherein said condensing step is carried out in the presence of an oxidizing agent.

18. The method of claim 1, wherein said condensing step is carried out in the presence of an oxidizing agent, and wherein said oxidizing agent is ambient oxygen.

19. The method of claim 1, wherein said condensing step is carried out at a temperature of 0 to 150° C.

20. The method of claim 1, wherein said condensing step is carried out for a time of 1 minute to 1 hour.

21. A method of making a porphyrin-metal complex, comprising:
  (a) providing a first reagent selected from the group consisting of 1,9-diacyldipyrromethanes and 1,9-diacyldipyrrins; and then
  (b) condensing said first reagent with a dipyrromethane in a reaction mixture comprising an solvent and a a second reagent selected from the group consisting of palladium and copper complexes to produce a porphyrin-metal complex, wherein said metal is selected from the group consisting of palladium and copper.

22. The method of claim 21, wherein said first reagent is a 1,9-diacyldipyrromethane.

23. The method of claim 21, wherein said first reagent is a 1,9-diacyldipyrrin.

24. The method of claim 21, wherein said second reagent is a copper 0, copper I, copper II, or copper III complex.

25. The method of claim 21, wherein said second reagent is a palladium 0, palladium II, or palladium IV complex.

26. The method of claim 21, wherein said second reagent is a palladium II or palladium IV complex.

27. The method of claim 21, wherein said second reagent is a palladium II or palladium IV complex selected from the group consisting of $PdX_2$, $PdX_2L_2$, $PdX_2L_4$, and $PdX_4Y_2Z_2$, wherein X is an anion, L is a neutral group; Y is a cation, and Z is an anion.

28. The method of claim 21, wherein said second reagent is a palladium II or palladium IV complex selected from the group consisting of: $K_2PdCl_6$, $Na_2PdCl_6$, $(NH_4)_2PdCl_6$, $Pd(OAc)_2$, $Pd(acac)_2$, $PdCl_2$, $PdBr_2$, $Pd(CN)_2$, $PdI_2$, PdO, $PdO.xH_2O$, PdS, $Pd(O_2CCF_3)_2$, $C_3H_5PdCl_2$, $(NH_4)_2PdCl_4$, $Pd(NO_3)_2.xH_2O$, $PdSO_4.H_2O$, $K_2PdBr_4$, $K_2PdCl_4$, $Na_2PdCl_4$, $K_2Pd(S_2O_3)_2.H_2O$, $(CH_3CO_2)_2Pd[P(C_6H_5)_3]_2$, $Pd(NH_3)_2(NO_2)_2$, $Pd(NH_3)_2(NO_3)_2$, $[Pd(NH_3)_4][PdCl_4]$, $Pd(NH_3)_2Cl_2$, $PdCl_2(CH_3CN)_2$, $PdCl_2[P(C_6H_5)_3]_2$, $PdCl_2(C_6H_5CN)_2$, $Pd(O_2CC_2H_5)_2$, $PdCl_2[P(C_6H_{11})_3]_2$, $PdCl_2[P(C_6H_5)_3]_2$, $PdCl_2[P(CH_3C_6H_5)_3]_2$, $Pd(BF_4)_2(CH_3CN)_4$, trans-di(μ-acetato)bis[o-(di-o-tolyl-phosphino)benzyl]dipalladium, dichloro(1,2-bis(diphenylphosphino)ethane)palladium(II), dichloro[1,1'-bis(diphenylphosphino)ferrocene] palladium(II)dichloromethane adduct, palladium(II) hexafluoroacetylacetonate, dichloro(1,5-cyclooctadiene) palladium(II), ammonium bis(oxalato)palladium(II), dichloro(ethylenediamine)palladium(II), bis(pyridine)palladium(II)chloride, chloro(di-2-norbornylphosphino)(2-dimethylaminomethylferrocen-1-yl)palladium(II), chloro(di-2-norbornylphosphino)(2'-dimethylamino-1,1'-biphenyl-2-yl) palladium(II), dichloro(1,3-bis(diphenylphosphino) propane)palladium(II), bis[tris(4-(1H, 1H,2H,2H-perfluorodecyl)phenyl)phosphine]palladium(II)dichloride, benzylbis(triphenylphosphine)palladium(II)chloride, (bicyclo[2.2.1]hepta-2,5-diene)dichloropalladium(II), ([2S,3 S]-bis[diphenylphosphino]butane)(eta$^3$-allyl)palladium(II) perchlorate, acetato(2'-di-t-butylphosphino-1,1'-biphenyl-2-yl)palladium(II), allylchloro[1,3-bis(2,6-di-isopropylphenyl)imidazol-2-ylidene]palladium(II).

29. The method of claim 21, wherein said second reagent is selected from the group consisting of $Pd(OAc)_2$, $Pd(acac)_2$, $Pd(CH_3CN)_2Cl_2$, $PdBr_2$ and $PdCl_2$.

30. The method of claim 21, wherein said solvent is an alcohol solvent, ethereal solvent, tetrahydrofuran, water, or mixture thereof.

31. The method of claim 21, wherein said solvent is ethanol.

32. The method of claim 21, wherein said reaction mixture further comprises a base.

33. The method of claim 21, wherein said reaction mixture further comprises a base selected from the group consisting of KOH and NaH.

34. The method of claim 21, wherein said reaction mixture has a pH of at least 7.

35. The method of claim 21, wherein said reaction mixture comprises not more than 0.5 percent by weight added acid.

36. The method of claim 21, wherein said condensing step is carried out in the presence of an oxidizing agent.

37. The method of claim 21, wherein said condensing step is carried out in the presence of an oxidizing agent, and wherein said oxidizing agent is ambient oxygen.

38. The method of claim 21, wherein said condensing step is carried out at a temperature of 0 to 150° C.

39. The method of claim 21, wherein said condensing step is carried out for a time of 1 minute to 1 hour.

* * * * *